US006696020B1

(12) United States Patent
Manz et al.

(10) Patent No.: US 6,696,020 B1
(45) Date of Patent: Feb. 24, 2004

(54) ELECTROCHEMILUMINESCENCE CELL WITH FLOATING REACTION ELECTRODES

(75) Inventors: Andreas Manz, East Molesey (GB); Arun Arora, London (GB)

(73) Assignee: Imperial College of Science, Technology and Medicine (GB)

( * ) Notice: Subject to any disclaimer, the term of this patent is extended or adjusted under 35 U.S.C. 154(b) by 0 days.

(21) Appl. No.: 09/743,485

(22) PCT Filed: Jul. 12, 1999

(86) PCT No.: PCT/GB99/02220
§ 371 (c)(1),
(2), (4) Date: May 7, 2001

(87) PCT Pub. No.: WO00/03233
PCT Pub. Date: Jan. 20, 2000

(30) Foreign Application Priority Data

Jul. 10, 1998 (GB) ............................................... 9815042

(51) Int. Cl.⁷ .............................................. G01N 21/76
(52) U.S. Cl. ................... 422/52; 422/87.01; 422/82.02; 422/82.03; 422/68.1; 436/149; 436/150; 436/172; 204/450; 204/451; 204/194

(58) Field of Search ................................ 422/52, 82.01, 422/82.02, 82.03, 68.1; 204/450, 451, 194; 436/149, 150, 172

(56) References Cited

FOREIGN PATENT DOCUMENTS

| EP | 0 388 990 A2 | 9/1990 |
|----|---|---|
| WO | WO 92/14138 | 8/1992 |
| WO | WO 96/28538 | 9/1996 |
| WO | WO 99/63347 | 12/1999 |

*Primary Examiner*—Jill Warden
*Assistant Examiner*—Sam P. Siefke
(74) *Attorney, Agent, or Firm*—Fay, Sharpe, Fagan, Minnich & McKee, LLP

(57) ABSTRACT

An electrochemiluminescence apparatus comprises a reaction vessel; means for generating an electric field (140, 160) within at least a region (120) of the reaction vessel; and one or more reaction electrodes (180) disposed in the electric field region of the reaction vessel, the reaction electrodes being arranged to float in or on a solution in the reaction vessel.

18 Claims, 23 Drawing Sheets

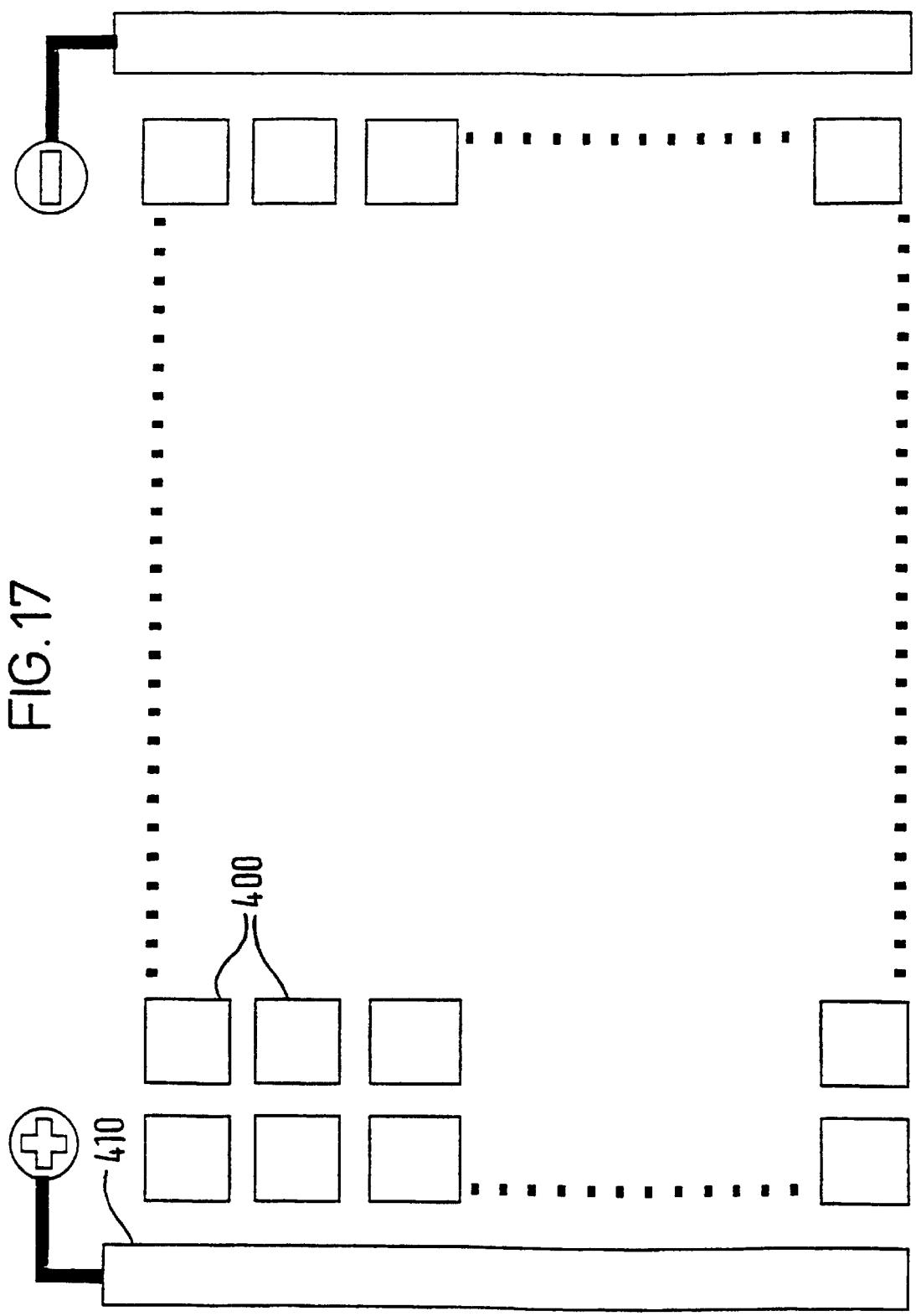

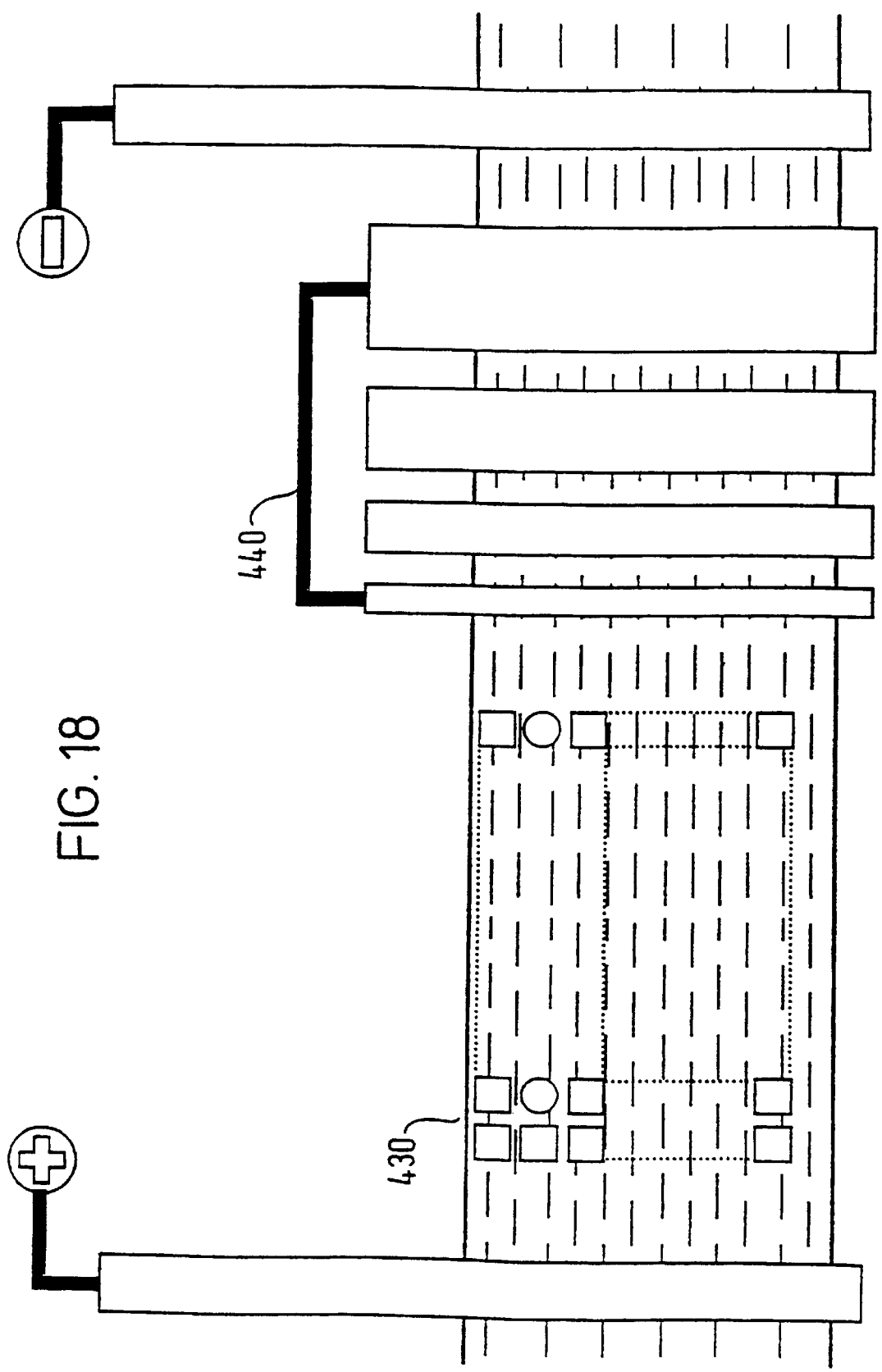

CONTINUOUS

DISCRETE PLUGS

SINGLE BEADS

ELECTROCHEMILUMINESCENCE CELL WITH FLOATING REACTION ELECTRODES This invention relates to detectors, for example so-called electrochemiluminescence detectors.

Electrochemiluminescence (ECL) is a highly specific and sensitive detection protocol used in a wide range of analytical reactions, These can include bioassay in clinical diagnostics and high throughput screening for drug discovery.

In ECL, light emission is believed to originate from the solution in vicinity of the electrode surface where the reacting species (alternatively generated at the electrode surface via a series of potential steps into the oxidation and reduction diffusion plateaux) recombine by electron transfer to give rise to a luminescent excited state. It is generally found that the ECL spectrum correlates very well with the solution luminescence spectrum for the species involved.

One example of the process behind ECL is schematically illustrated in FIG. 1 of the accompanying drawings. Both tris(2,2'-bipyridyl) ruthenium (II) (TBR—also illustrated on FIG. 1 as $Ru(bpy)_3$) and tripropylamine (TPA) are oxidised in aqueous solution at an anode face 10 of an electrode 40. The TPA is unstable and becomes deprotonated almost immediately to form TPA'. Subsequent electron transfer between TPA' and $TBR^+$ molecules leads to the formation of DPA (dipropylamine) and excited state TBR molecules (TBR*), which then relax radiatively to the ground state via an optical emission at a wavelength of 610 nm. In this reaction, although TPA is consumed, the TBR is recycled.

The arrangement shown in FIG. 1 is a so-called bipolar electrode design. In this arrangement, two end electrodes 20, 30 are connected to a power supply, with electrical continuity between them being provided by conduction through the aqueous electrolyte. Other intermediate electrodes (of which one, the electrode 40, is illustrated in FIG. 1) are not directly connected (i.e. wired) to the power supply but instead function as an anode on one face and a cathode on the other. So, every two adjacent electrodes and the intervening solution function as a reactor unit, with the overall apparatus forming a series connection of such reactor units. This arrangement is described in the book, "Electrochemical Reactor Design", D J Pickett, Elsevier Scientific Publishing Company, 1979, and the chemical process is described in the article, "Sub-Microlitre Electrochemiluminescence Detector—A Model for Small Volume Analysis Systems", A Arora et al, Analytical Communications, 34, pp 393–395, 1997. This article also describes an ECL detection apparatus specifically for use with small sample volumes, the apparatus comprising a flow channel cut into an acetate sheet sandwiched between two blocks of poly (methyl methacrylate) or PMMA. Platinum foil strips are secured across the flow channel by the sandwich structure for use as the electrodes.

This invention provides an electrochemiluminescence apparatus comprising:
  a reaction vessel;
  means for generating an electric field within at least a region of the reaction vessel; and
  one or more reaction electrodes disposed in the electric field region of the reaction vessel, the reaction electrodes being arranged to float in or on a solution in the reaction vessel.

In apparatus according to the invention, a novel type of electrode is used in an electrochemiluminescence technique, namely a floating electrode. This has many advantages over previous systems. The floating electrodes can be isolated or electrically short-circuited, and their use allows complex electrode patterns (such as extensive 1-, 2- or 3-dimensional electrode arrays) to be constructed on a very small physical scale, so allowing detection volumes to be very small while still providing useable emission light levels.

Potential uses of this technique and apparatus include immunoassays, DNA binding assays, receptor based assays, cell based assays, as a detector in liquid chromatography, for electrophoresis, electrochromatography in clinical diagnostics, enviroinental analysis, and in pharmaceutical and chemical research analysis.

The hydrostatically floating electrodes described above could also be electrically floating with respect to the means for providing an electric field, but need not be so. The invention also provides an electrochemiluminescence apparatus comprising: a reaction vessel; means for generating an electric field within at least a region of the reaction vessel; and one or more reaction electrodes disposed in the electric field region of the reaction vessel, the reaction electrodes being arranged to be electrically floating with respect to the means for generating the electric field.

Preferably, the apparatus comprises first and second supply electrodes connectable to an electrical power supply, the supply electrodes being disposed with respect to the reaction vessel and with respect to one another so that an electric current can flow between the electrodes through a conductive solution in the reaction vessel; the one or more reaction electrodes being disposed in the reaction vessel in a current flow path between the supply electrodes.

In this aspect of the invention, the reaction electrodes are electrically floating. That is to say, they are not connected directly to the power supply electrodes, apart from via their surroundings such as a conductive solution in the vessel. In this case, the reaction electrodes can be hydrostatically floating as well, could be fixed with respect to the vessel, or could be untethered but of such a nature that they sink.

Embodiments of the invention will now be described, by way of example only, with reference to the accompanying drawings in which:

FIG. 1 schematically illustrates a previously proposed bipolar electrochemical flow cell;

FIG. 2 schematically illustrates an electrochemical flow cell according to an embodiment of the invention;

FIG. 3 schematically illustrates an operational configuration for the flow cell of FIG. 2;

Figure 1:
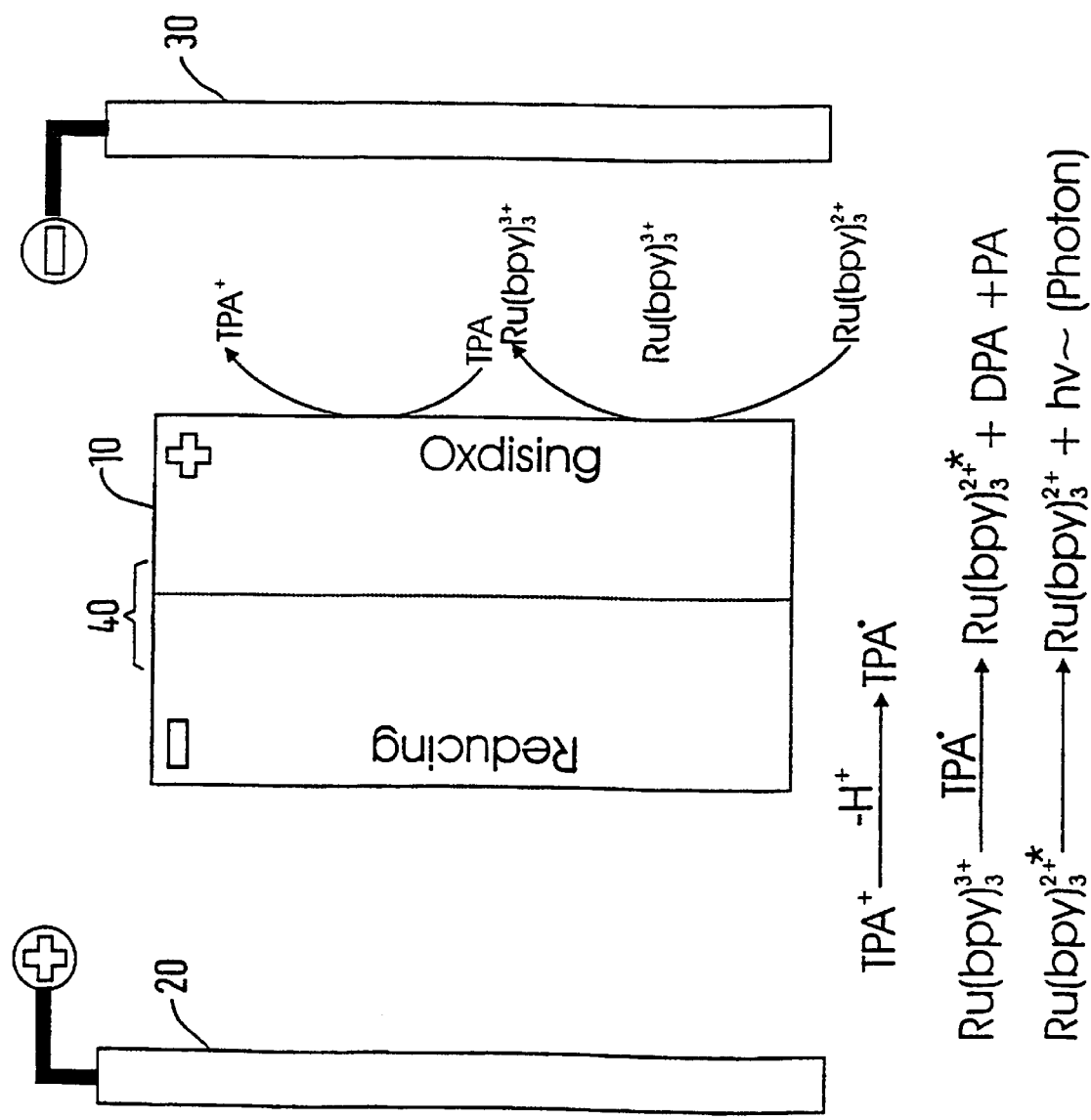
Figure 2:
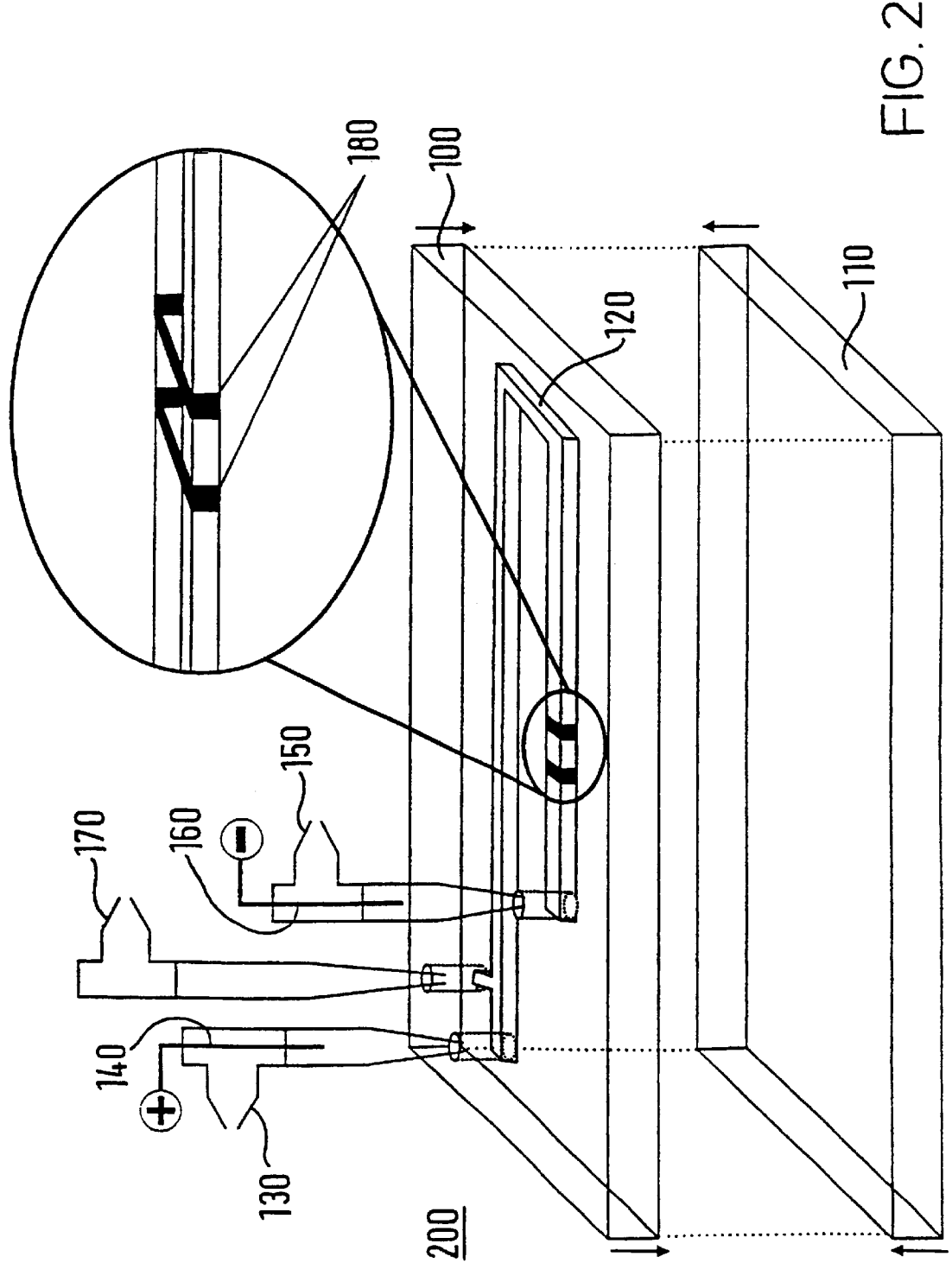
Figure 6:
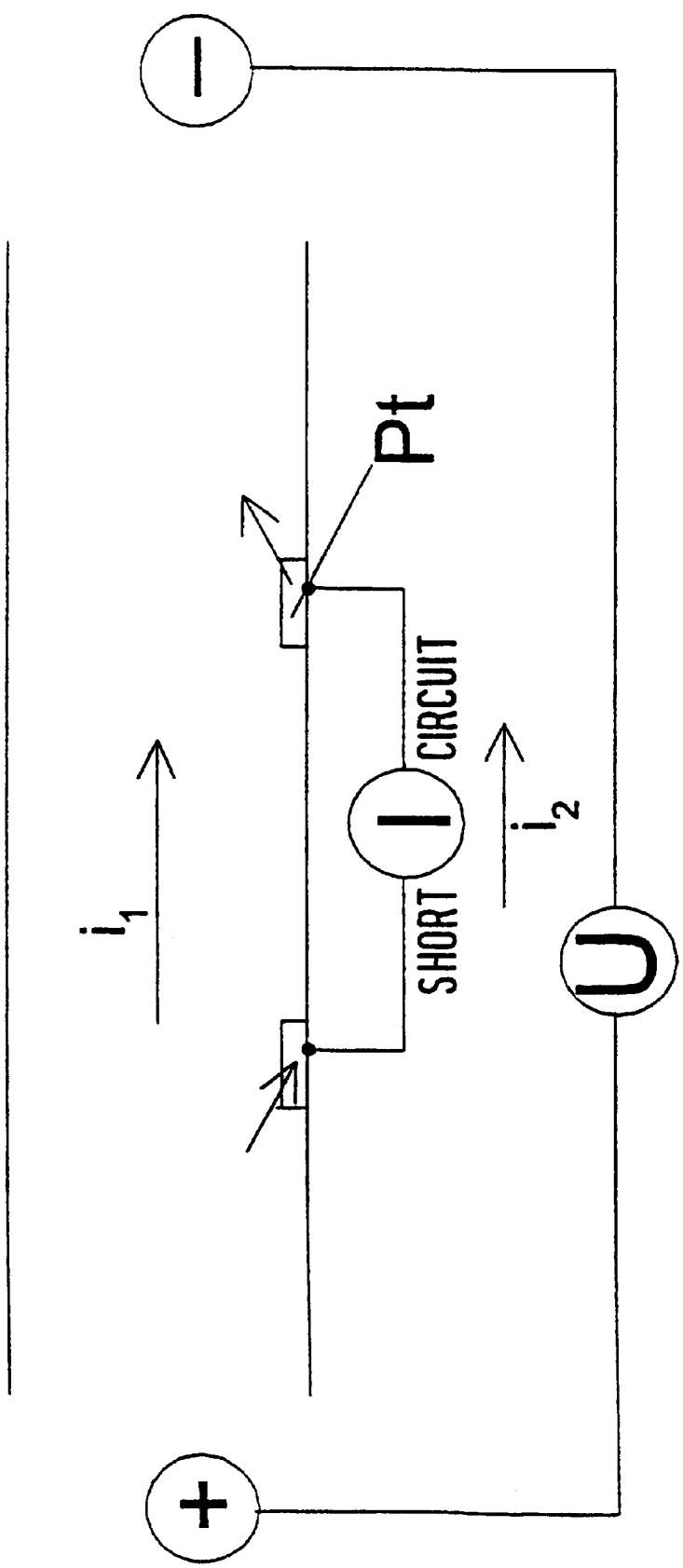
Figure 7:
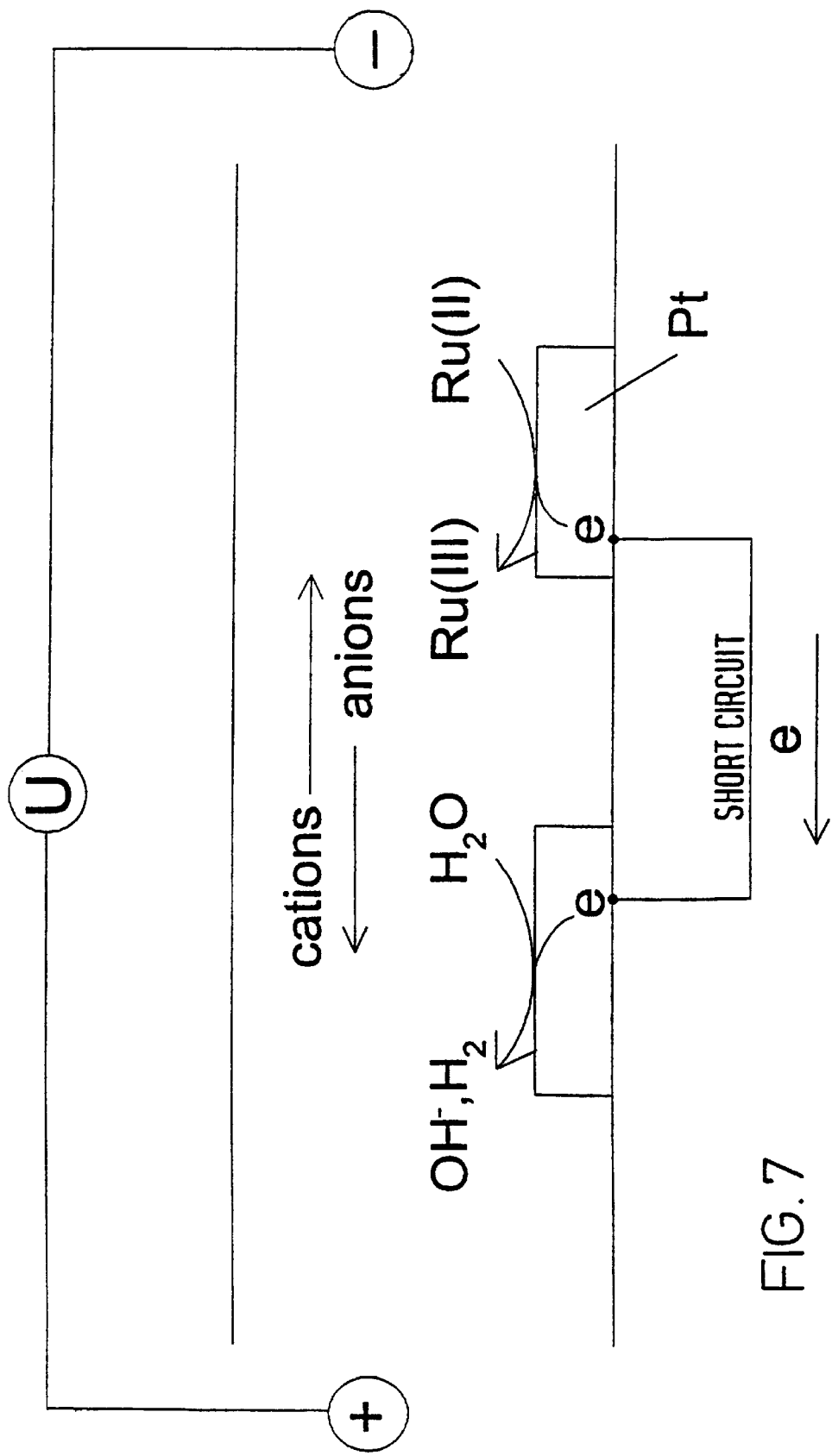
Figure 8:
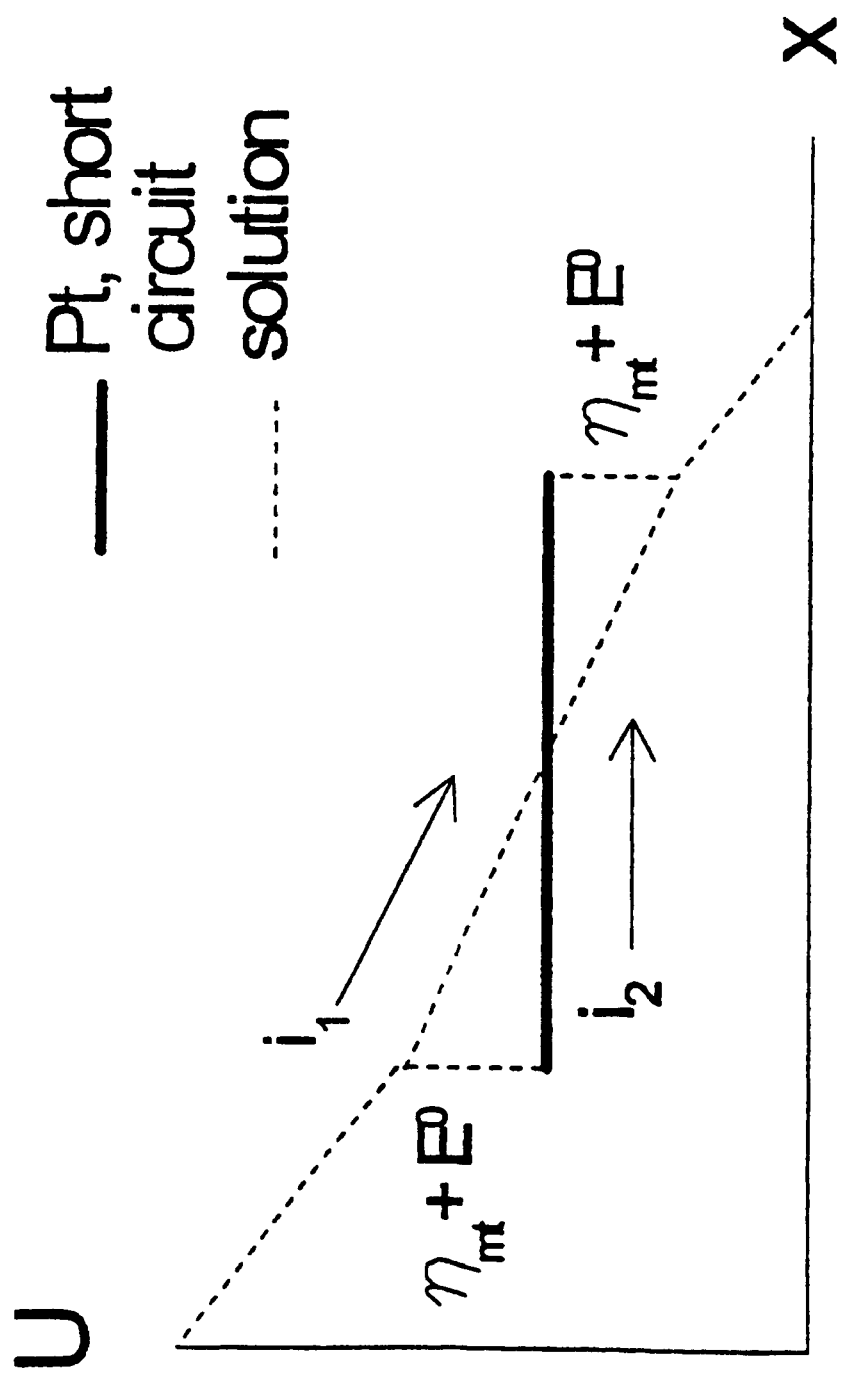
Figure 9:
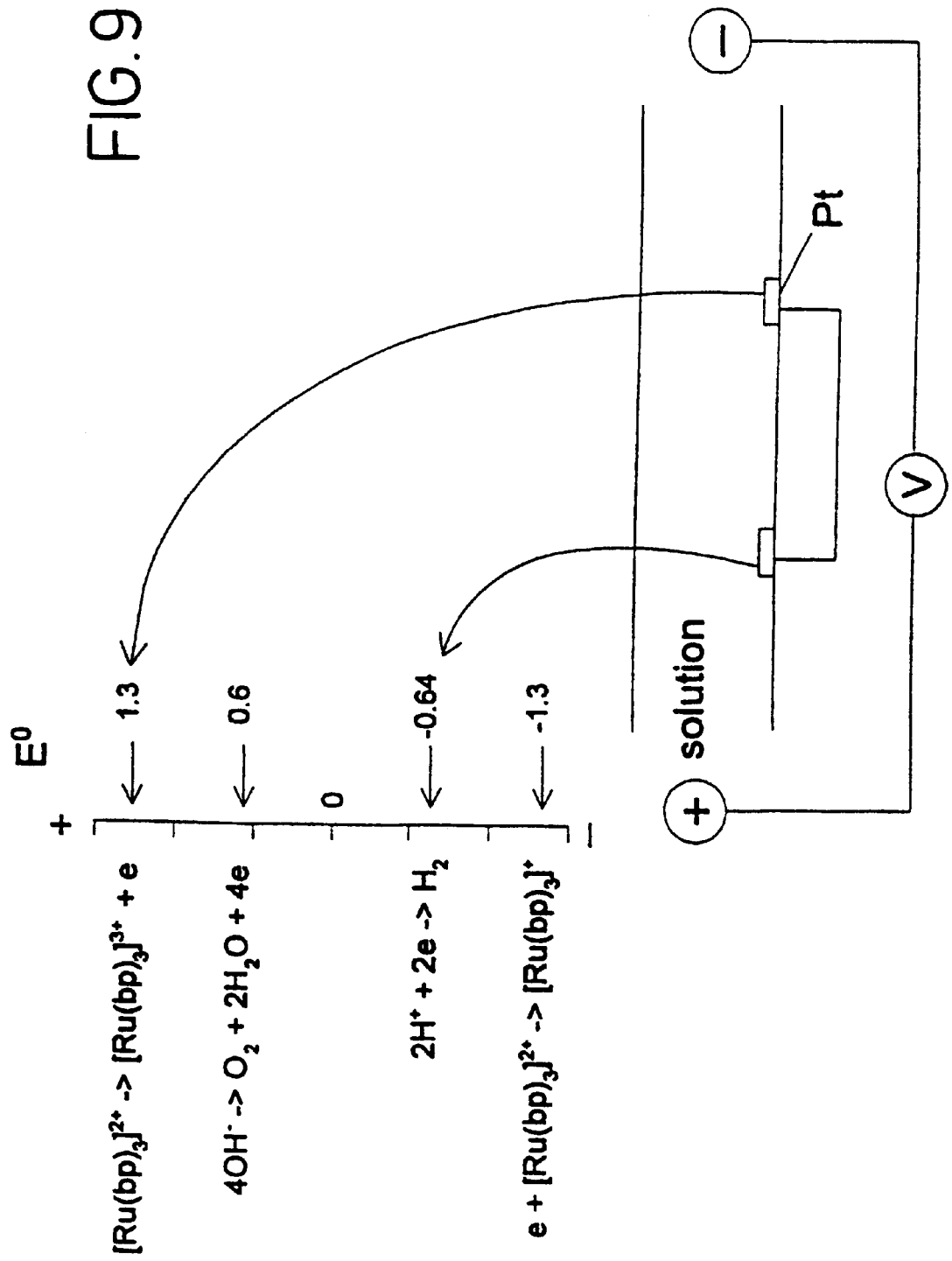
Figure 10:
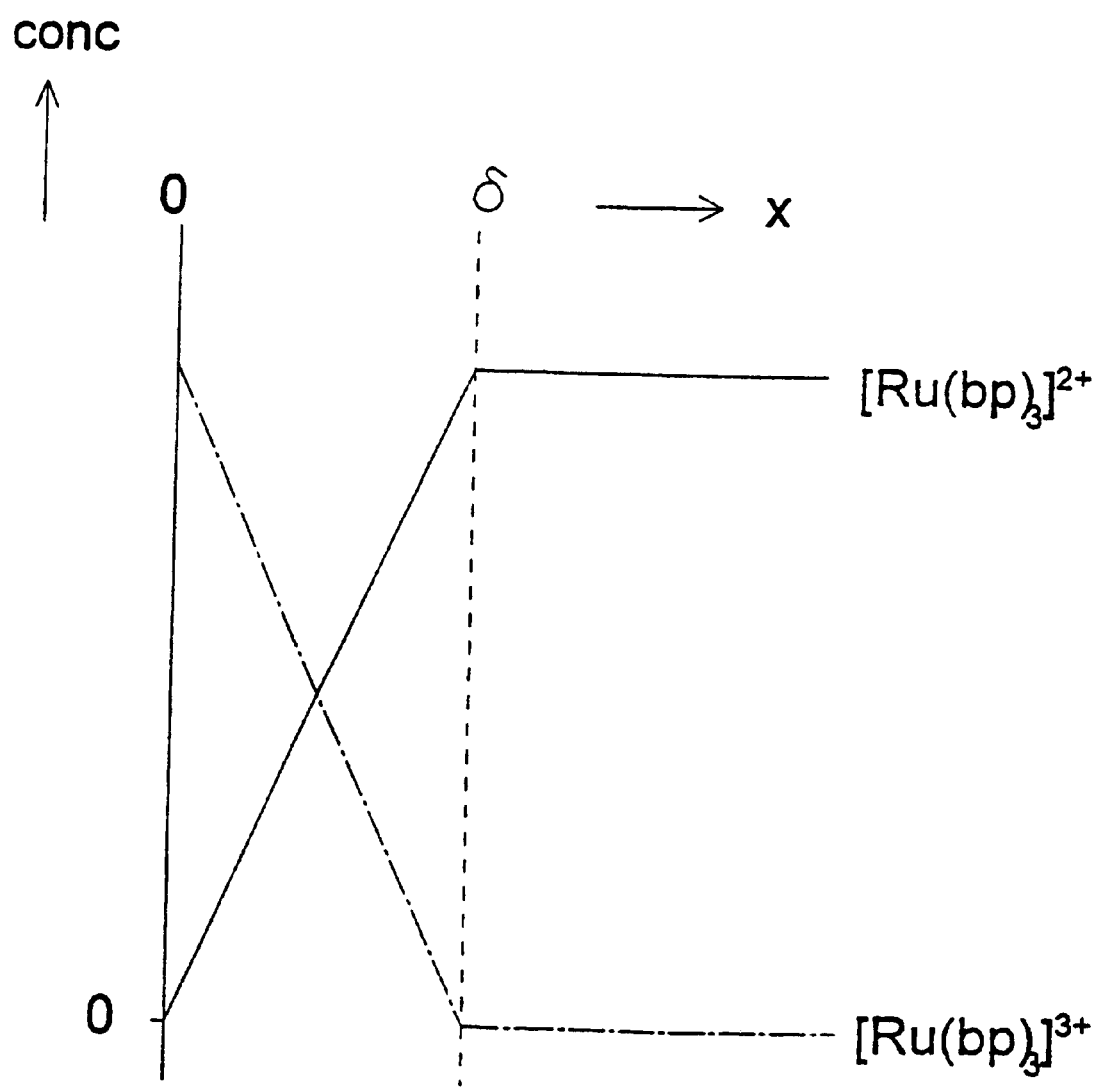
Figure 11:
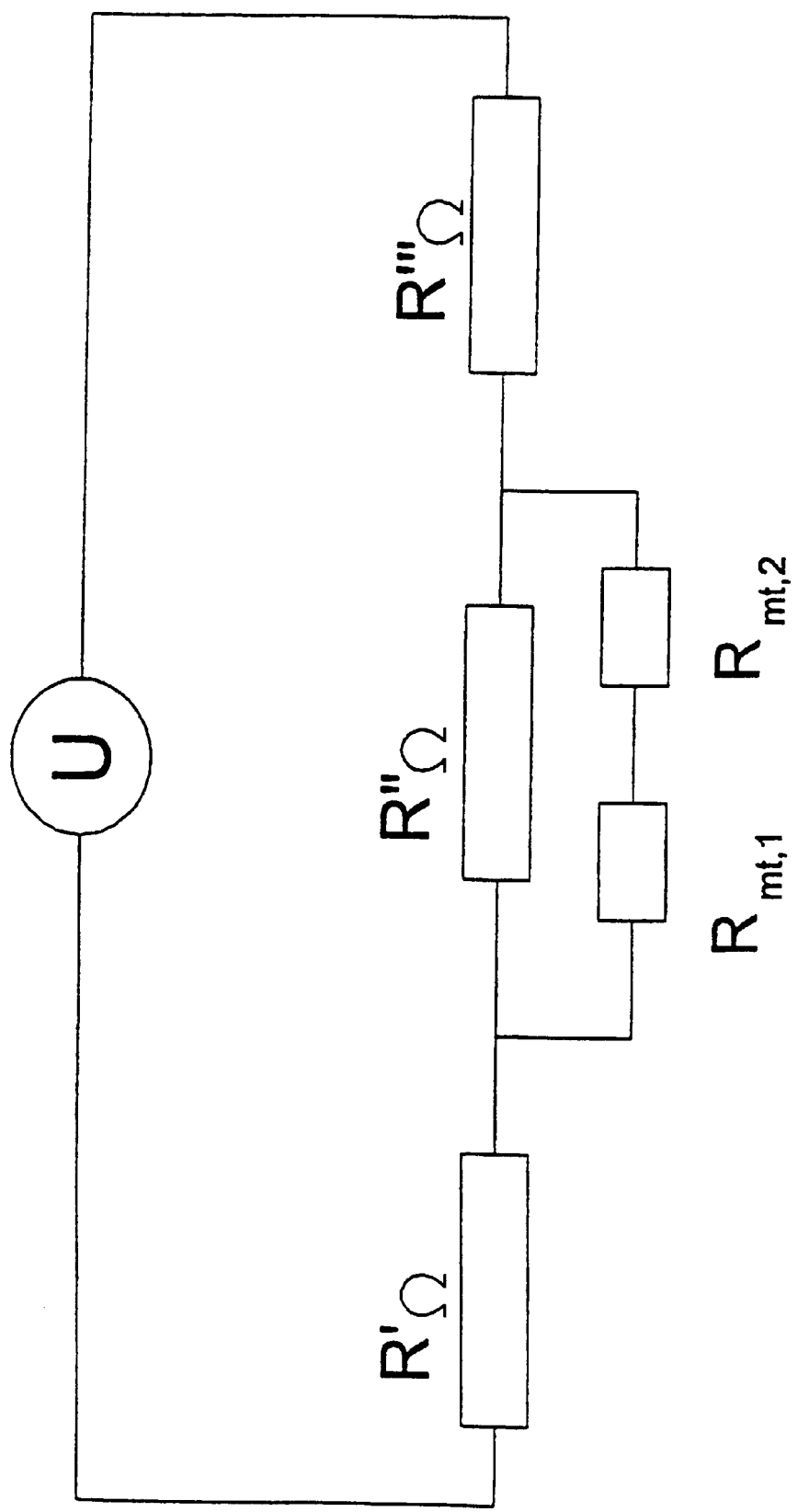
Figure 12:
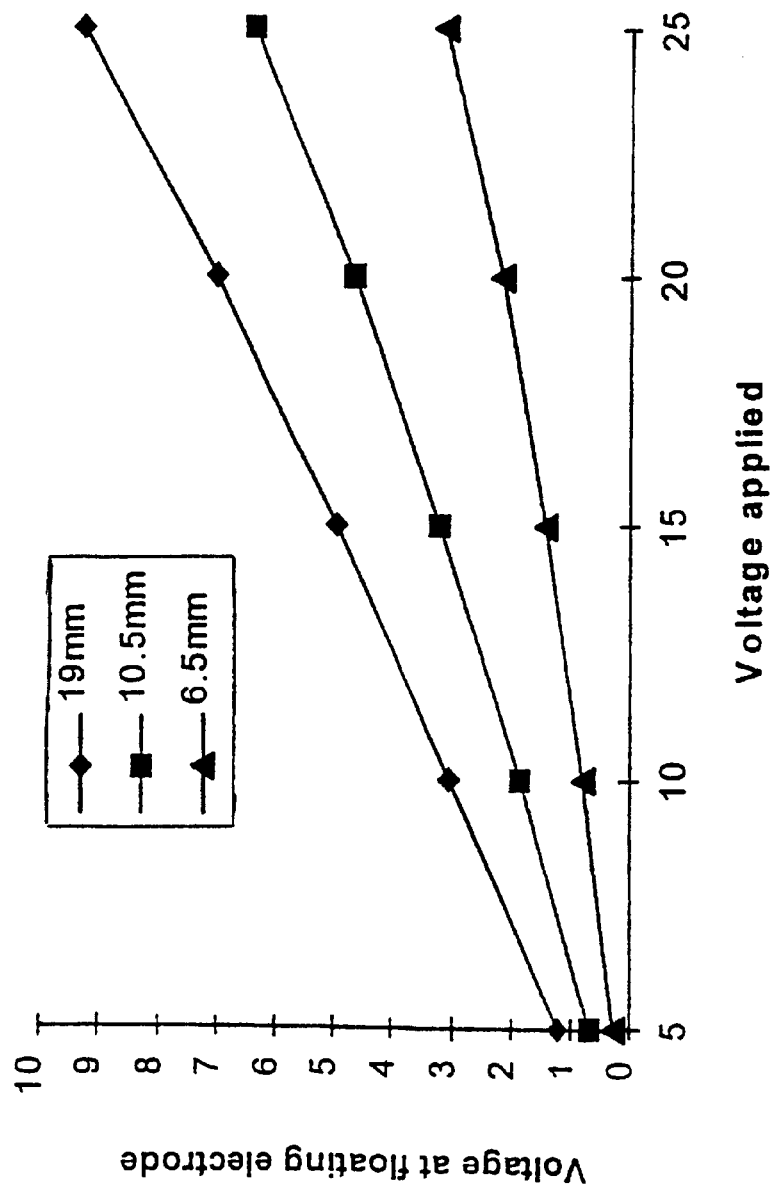
Figure 13:
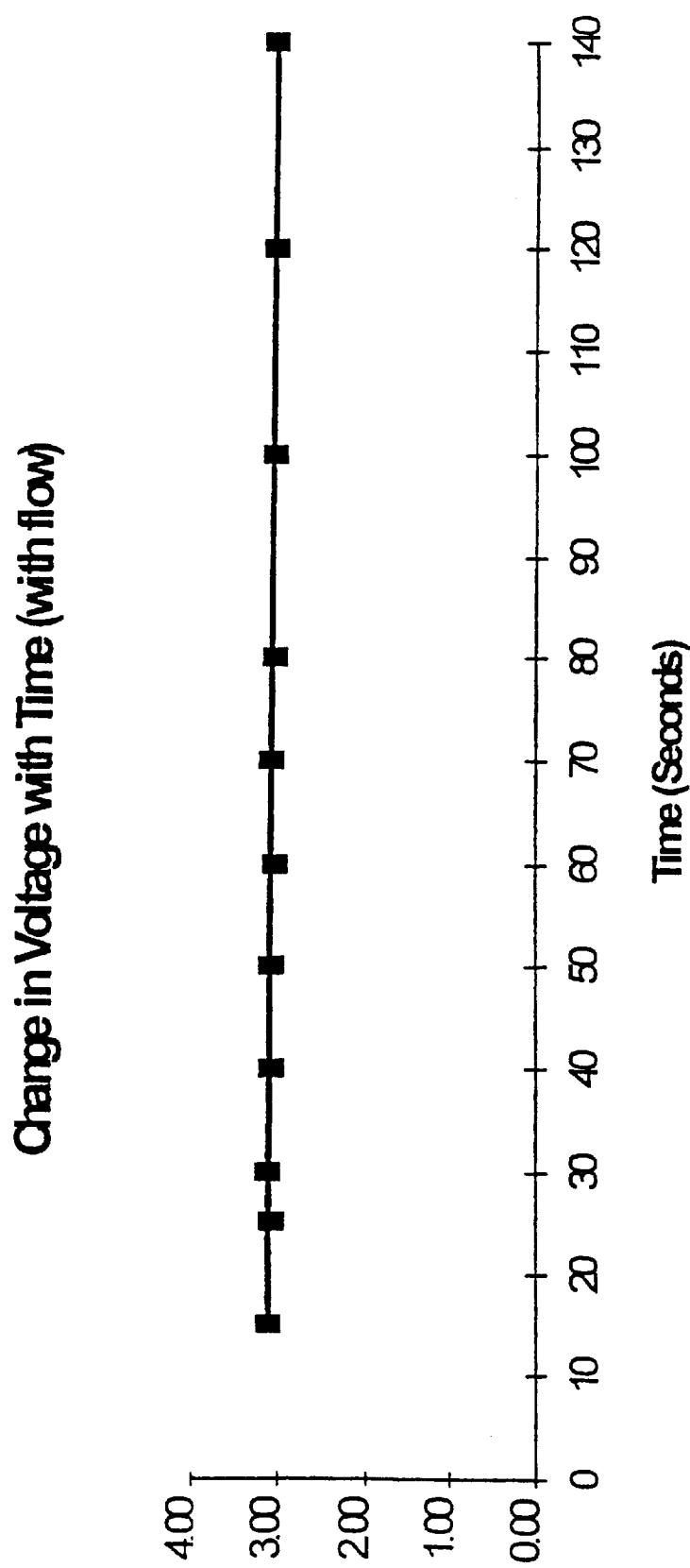
Figure 14:
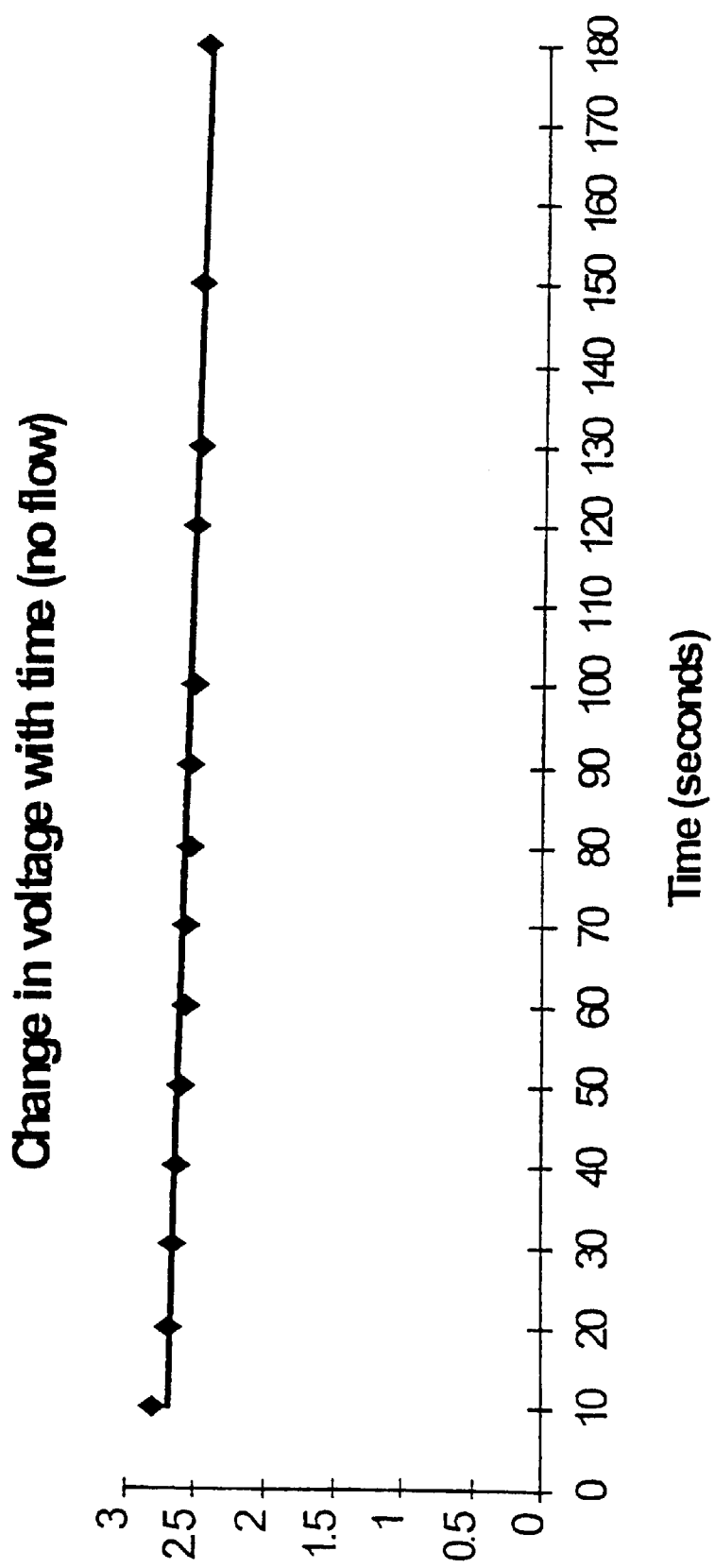
Figure 15:
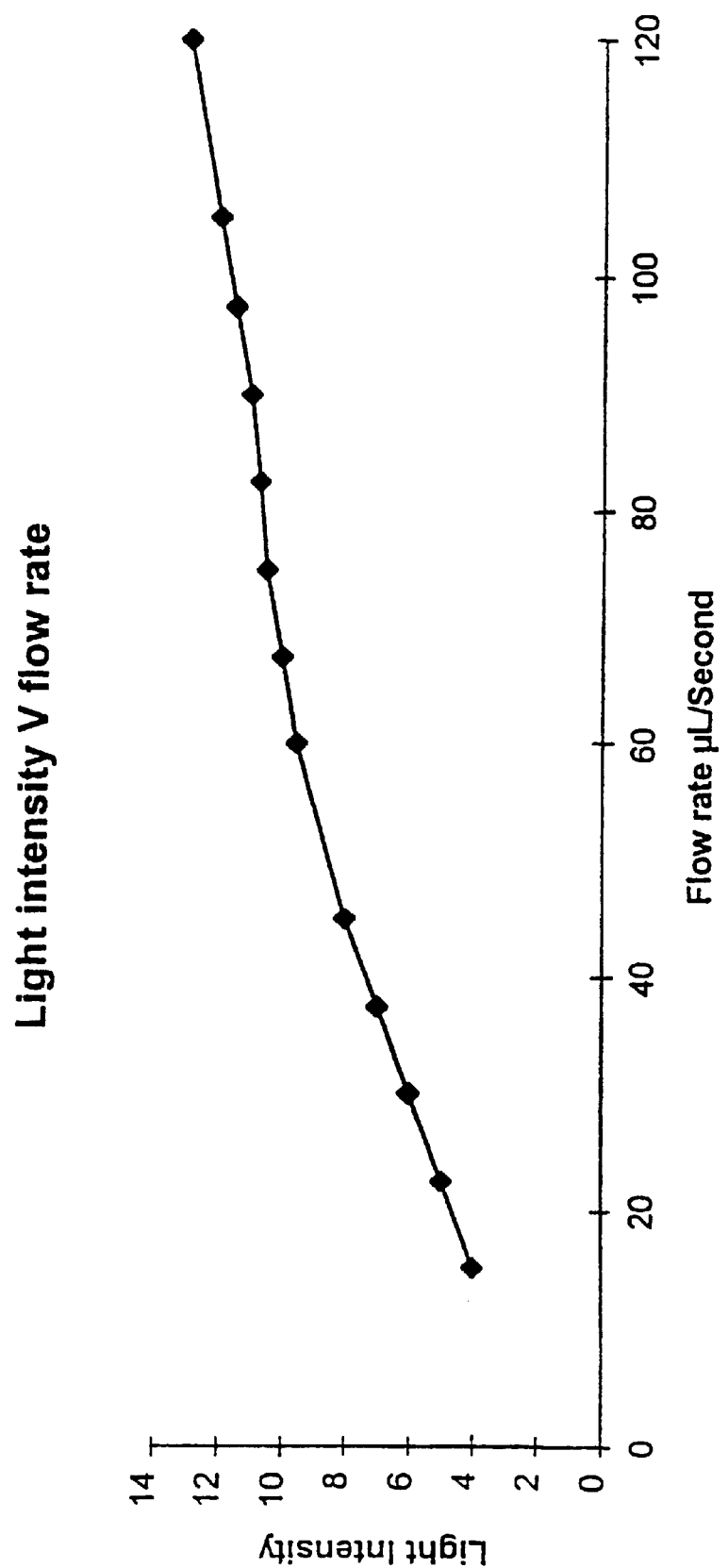
Figure 16:
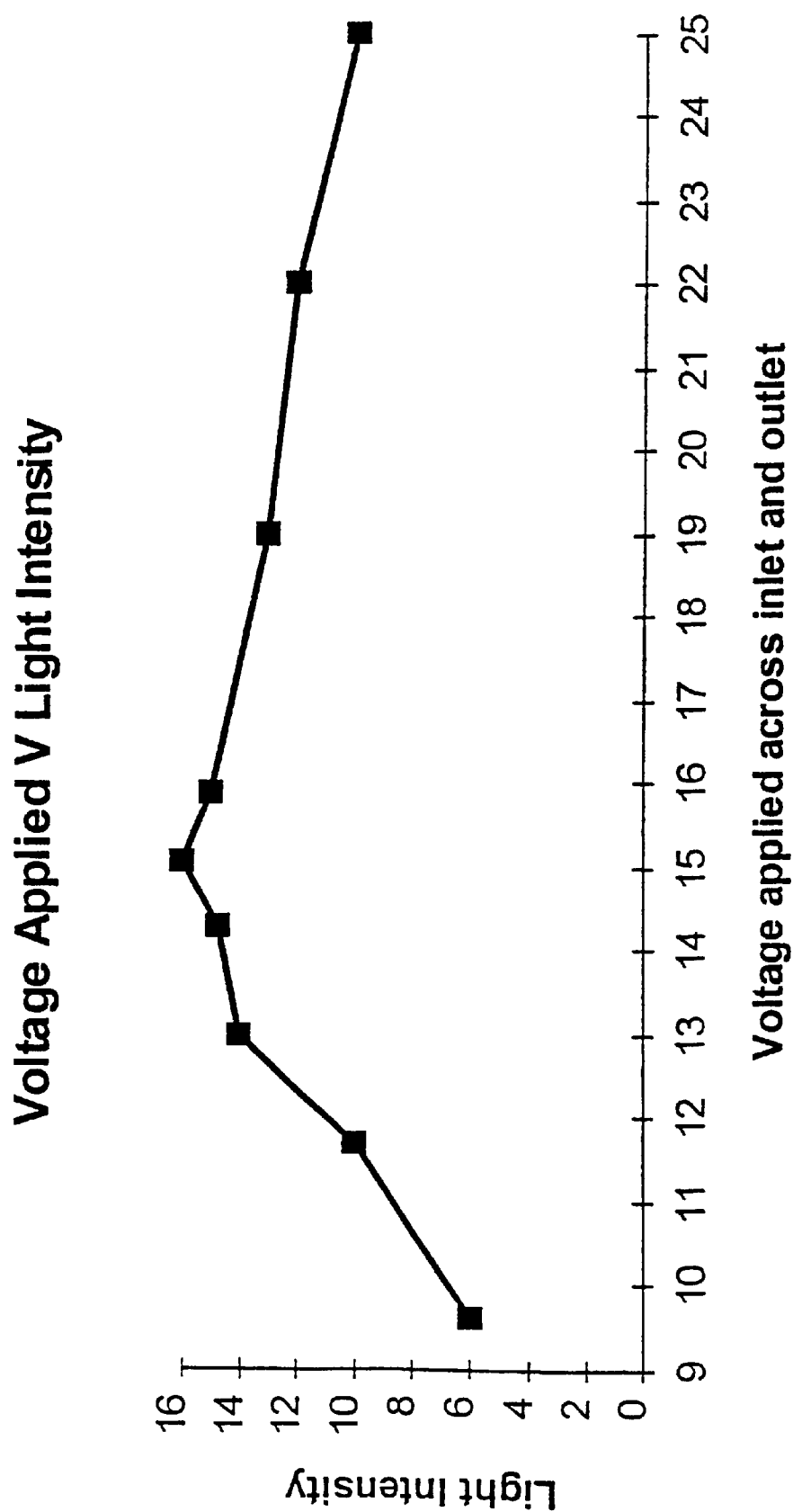
Figure 19A:
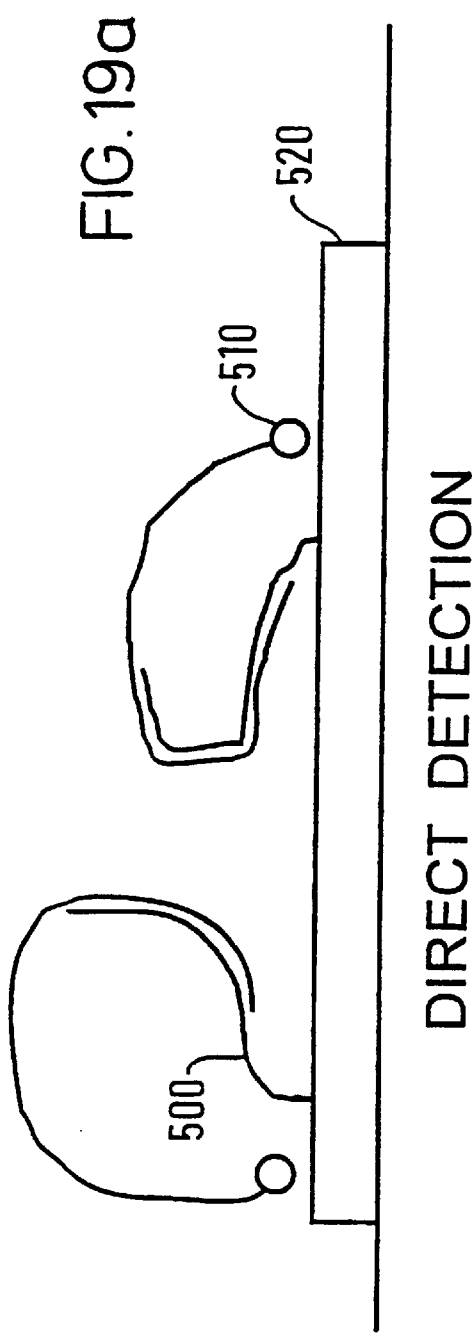
Figure 19B:
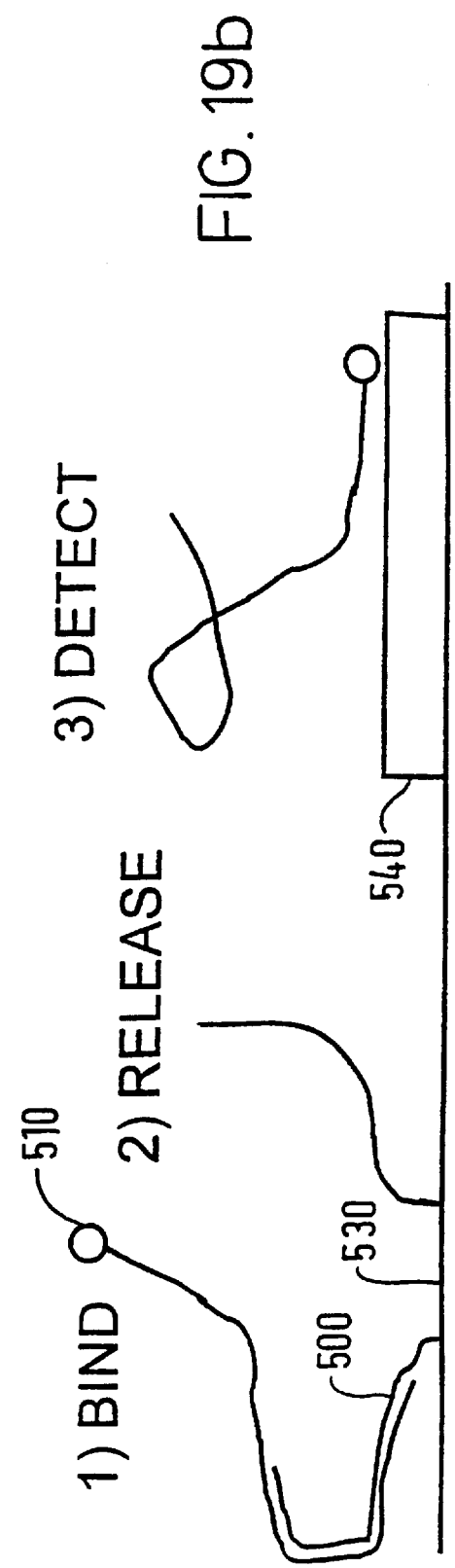
Figure 20:
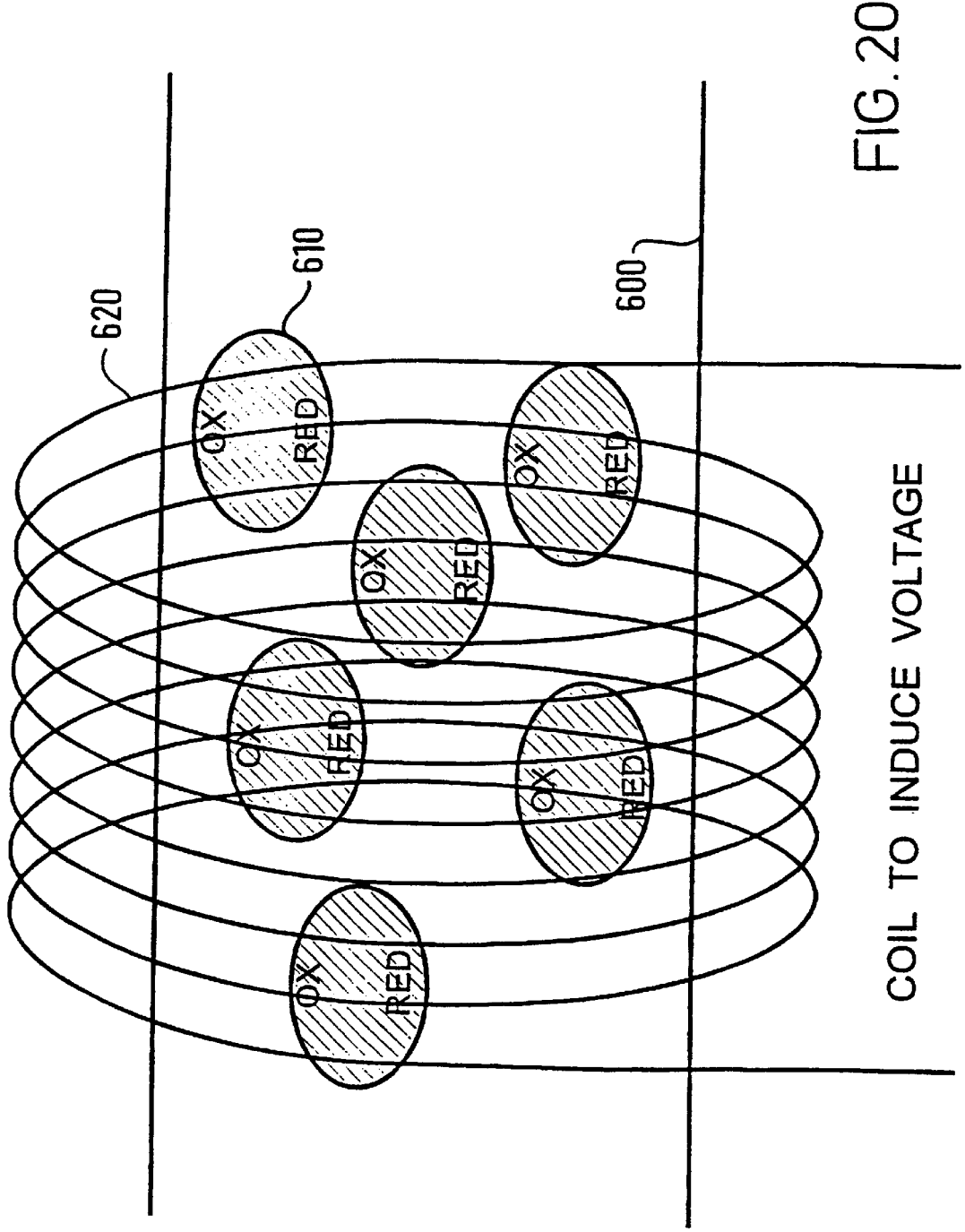
Figure 21:
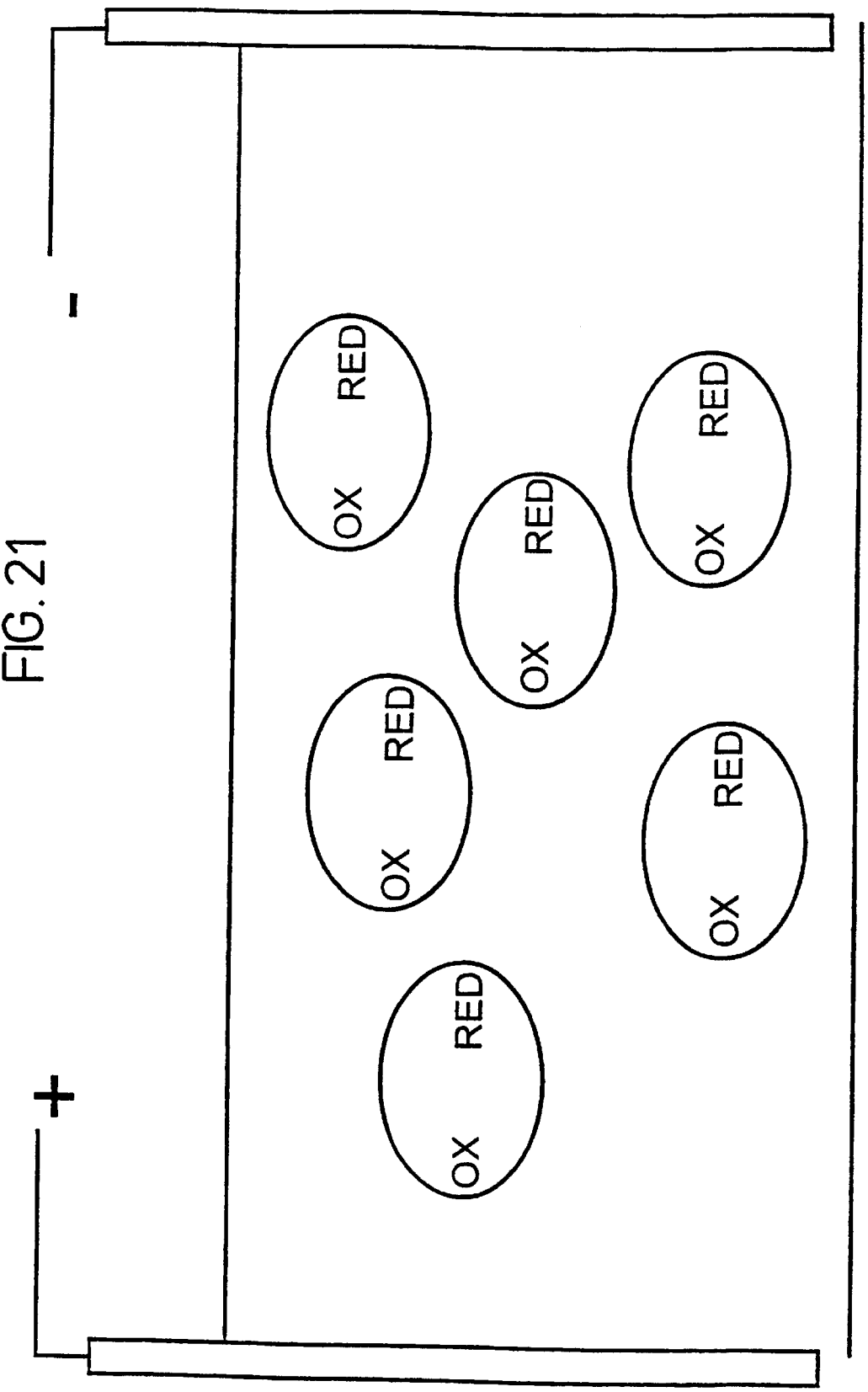
Figure 22A:
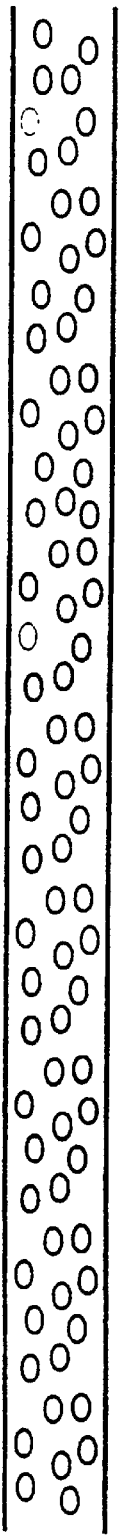
Figure 22B:
Figure 22C:
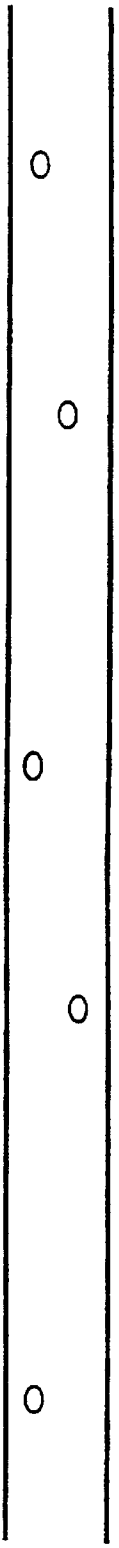
Figure 23:
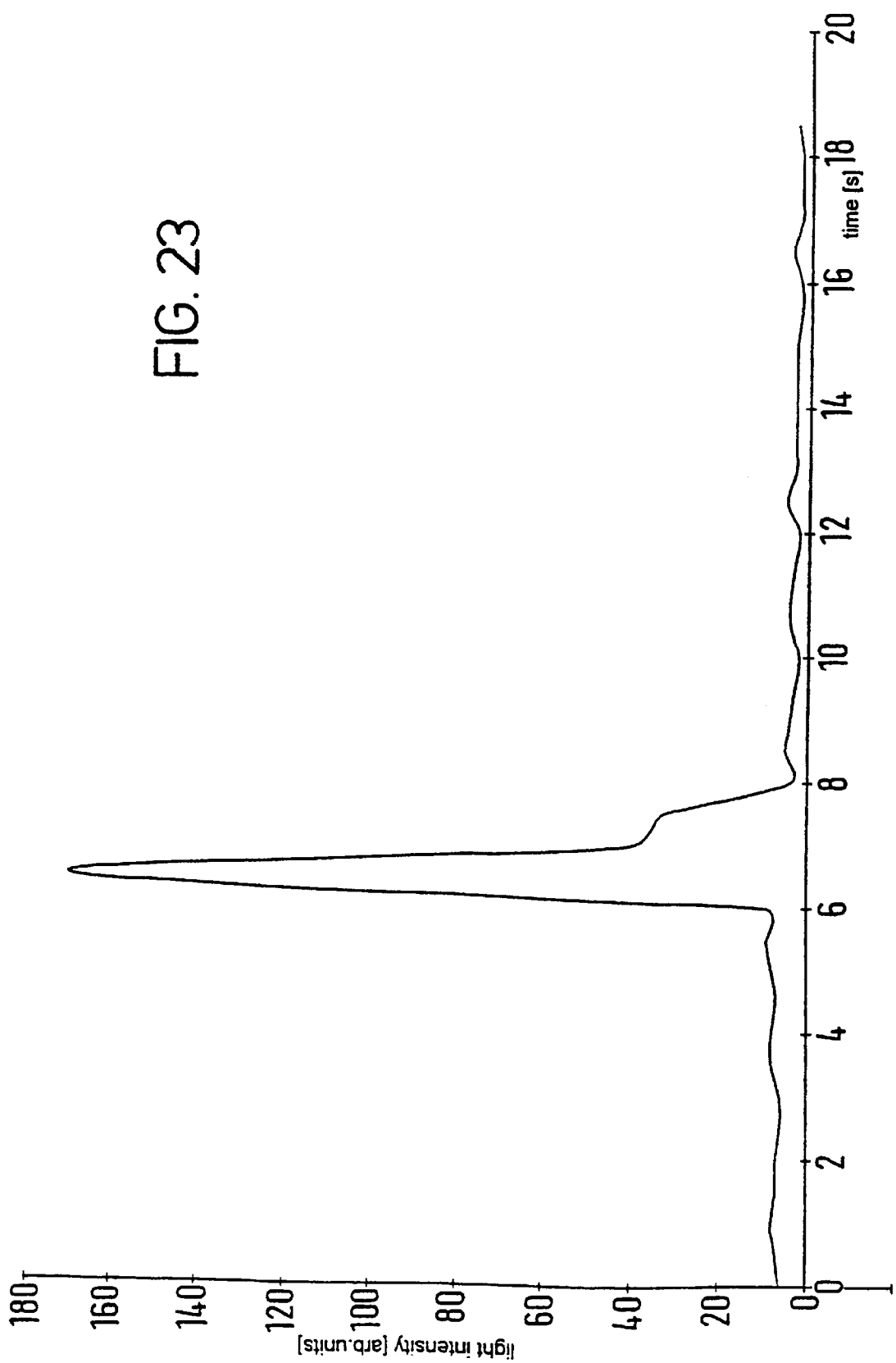

FIG. 6 schematically illustrates current flow through the floating electrodes in the flow cell of FIG. 2;

FIG. 7 schematically illustrates cation and anion fluxes in the flow cell of FIG. 2;

FIG. 8 schematically illustrates current flows $i_1$ and $i_2$ through the solution and electrodes respectively in the flow cell of FIG. 2;

FIG. 9 schematically illustrates the process of oxidation of ruthenium occurring at the anode;

FIG. 10 schematically illustrates the concentration of ruthenium in the Nernst diffusion layer at the anode;

FIG. 11 schematically illustrates an equivalent electrical circuit;

FIG. 12 is a graph of voltage variation against distance between the floating electrodes;

FIG. 13 is a graph of voltage variation against time for a flowing solution;

FIG. 14 is a graph of voltage variation against time for a non-flowing to solution;

FIG. 15 is a graph of light intensity against flow rate;

FIG. 16 is a graph of light intensity against applied voltage;

FIG. 17 is a schematic plan view of another embodiment;

FIG. 18 is a schematic side elevation of a further embodiment;

FIG. 19a schematically illustrates a DNA binding assay in a direct detection arrangement;

FIG. 19b schematically illustrates a DNA binding assay in an indirect detection format;

FIG. 20 illustrates an embodiment using inductive generation of an electric field in a reaction vessel;

FIG. 21 schematically illustrates the use of particulate electrodes;

FIGS. 22a to 22c schematically illustrate three different configurations using particulate electrodes; and FIG. 23 schematically illustrates results obtained from a combined electrochemiluminescence and electrophoresis apparatus.

In the following description (though not in the claims) the term "floating" should be taken to read "hydrostatically and electrically floating" unless the context clearly precludes this. The majority of the embodiments below do involve hydrostatically and electrically floating electrodes, but within the scope of the invention other embodiments can be either hydrostatically floating or electrically floating but not both.

In the embodiments to be described below, floating platinum (Pt) electrodes disposed in an electric field are used to generate the electrochemiluminescence from the reaction of tris(2,2'-bipyridyl) ruthenium (II) dichloride hexahydrate (TBR) and Tripropyl Amine (TPA). In particular, the voltage required to oxidise $Ru^{2+}$ to $Ru^{3+}$ on the surface of the working electrode is provided by arranging floating electrodes in a solution flow channel and applying a dc voltage across the inlet and outlet of the channel.

The floating electrodes can be for example: a loose piece of metal wire, metal particles, mercury droplets, a layer of metal foil and so on. Basically, the technology needed to make an item float has been established for millennia, so it is well within a routine design process by the skilled man to produce an electrode formation which is capable of floating on a liquid. To avoid doubt, it will also be appreciated that the term "float" does-not specify how much of an object sits below the liquid's surface—clearly this will depend on the design and nature of the floating item. Indeed, it is of course not a requirement that any of the body of the electrode protrudes above the liquid surface. The electrodes may float in suspension, in the same way that a submarine can float at a particular depth under the sea's surface.

The electrodes can be made of a single metal or other electrical conductor, or can be formed of an alloy or a coated structure.

A PMMA flow cell with Pt electrodes was constructed as a prototype, and is illustrated schematically in FIG. 2.

The flow cell is formed of two sheets of PMMA 100, 110 sandwiched together (they are shown separated in the drawing for clarity). In one PMMA sheet, the sheet 100, a channel 120 is engraved.

A solution inlet 130 contains a platinum electrode 140 connected to a power supply (not shown) and acting as an anode. Similarly a solution outlet 150 contains a platinum electrode 160, also connected to the power supply and acting as a cathode. A sample injection port 170 also communicates with the channel and allows the injection of samples under test.

Two floating platinum electrodes 180 are provided, spaced along the channel in a flow direction. These electrodes are short-circuited together by a metal wire (not shown). They can be tethered or untethered with respect to the channel. (In other embodiments, they may be fixed with respect to the channel so that they are electrically floating but not hydrostatically floating. The electrodes should have at least one "floating" property, i.e. electrically floating, hydrostatically floating or both).

Some particular specifications of the PMMA flow cell are as follows: channel length between cathode and anode: 76 mm channel width: 1 mm channel height: 0.1 mm width of floating Pt electrodes: 1 mm separation of Pt electrodes: 6 mm voltage applied: 15–20 volts solutions: $10^{-4}$ down to $10^{-8}$ molar (2,2' bipyridyl) ruthenium (II) chloride and $5 \times 10^{-3}$ molar TPA in a phosphate buffer.

Figure 3:
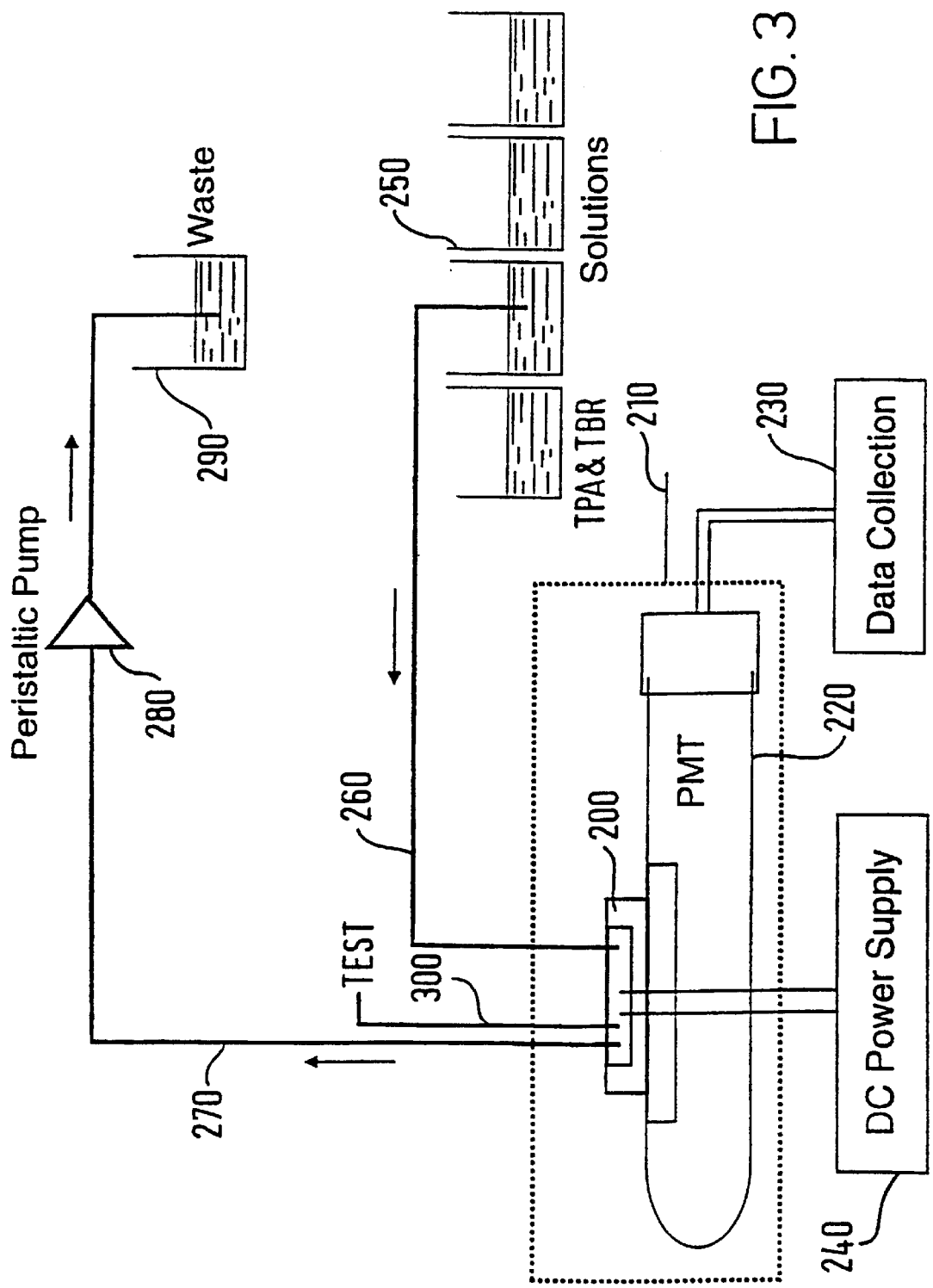

FIG. 3 schematically illustrates an operational configuration for the flow is cell of FIG. 2.

The flow cell 200 is encased in a light-tight wooden box 210 along with a photomultiplier tube (PMT) 220 connected to conventional data collection circuitry 230. Light-tight fluid and electrical connections are provided.

The anode 140 and cathode 160 are connected to a direct current (dc) power supply 240. The fluid inlet 130 is connected to a supply of TPA and TBR solution 250 via a silicone tube 260. The fluid outlet 150 is connected by silicone tube 270 to a peristaltic pump 280 and from there to a waste outlet. The sample injection port 170 is connected via a silicone tube 300 to the exterior of the wooden box so that samples under test can be injected into the flow cell.

Figure 4:
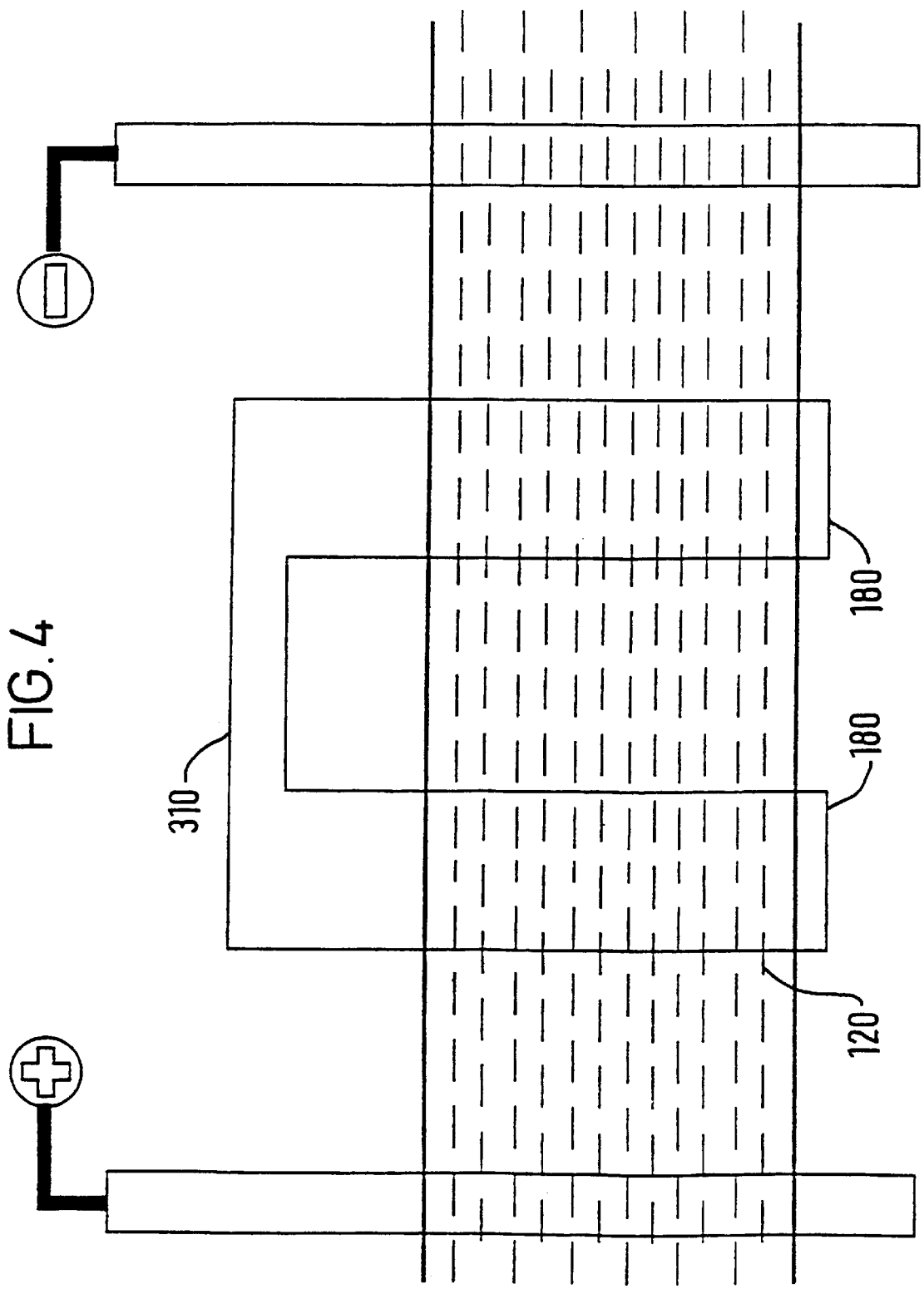
FIG. 4 is a schematic cross-section through a channel in the flow cell of FIG. 2.

FIG. 4 is a schematic cross-section through the channel 120 showing two floating electrodes 180 short-circuited together by an electrical connection 310. The channel 120 contains TBR and TPA solution.

Figure 5:
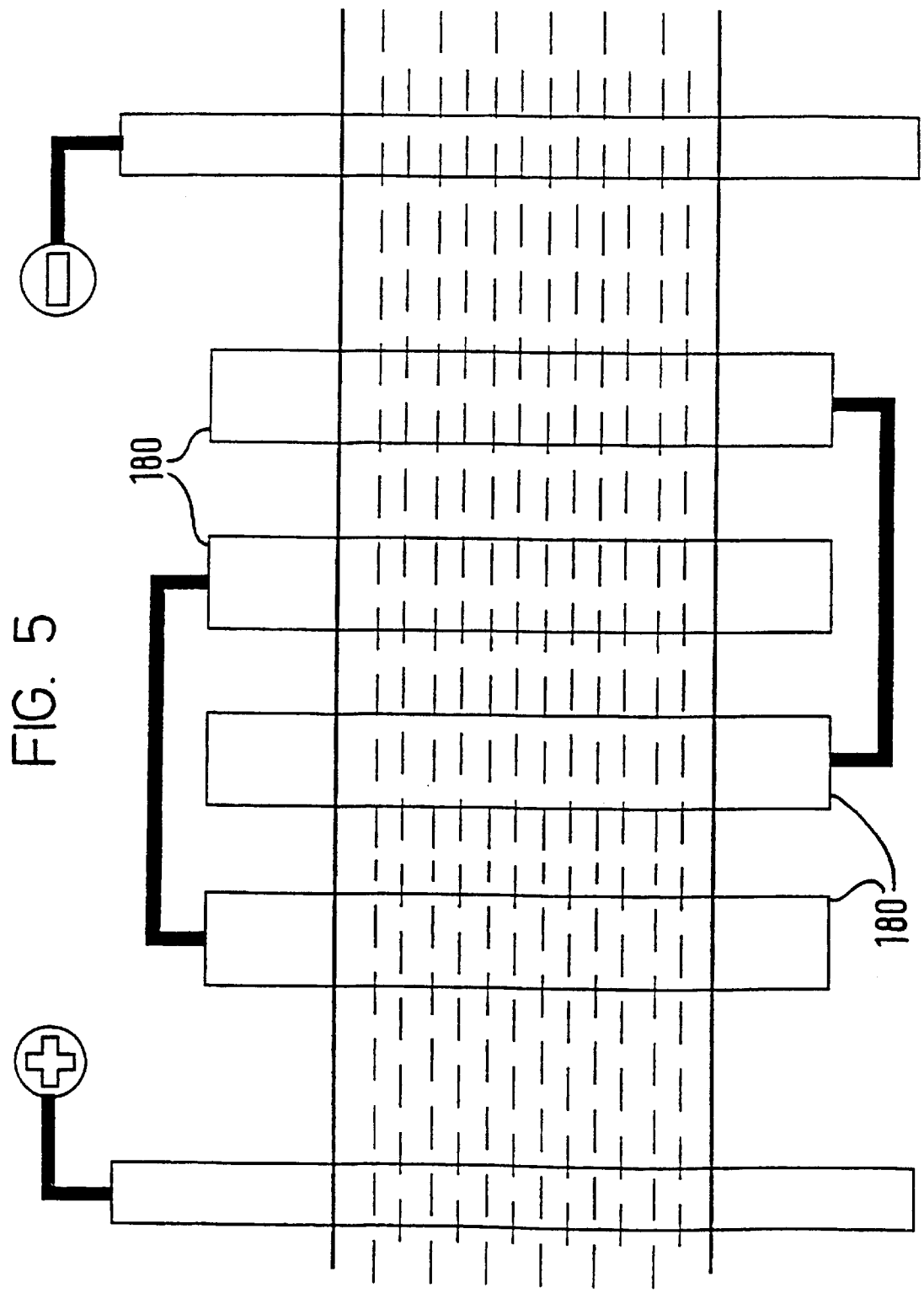
FIG. 5 is a schematic cross-section through a channel in an alternative form of the flow cell of FIG. 2.

FIG. 5 illustrates an alternative arrangement of four electrodes 180 short-circuited in alternate pairs.

The theoretical background behind the operation of the flow cell will now be described, and then some performance results will be given for prototype embodiments.

Theoretical Background

When a potential U is applied along the channel, a current i results through the electrolyte. The floating platinum electrodes locally offer an alternative current path, giving rise to two parallel currents $i_1$ (solution) and $i_2$ (platinum electrodes), as illustrated schematically on FIG. 6.

FIG. 7 schematically shows the processes that cause the current flow. In the solution they are the summated fluxes of all anions towards the anode and of all the cations towards the cathode. In the platinum electrode short circuit, the current is carried by electrons.

Faradeic processes at the interfaces of electrode and solution convert the electronic ionic fluxes into an electronic flow. FIG. 7 shows that the floating electrode that is closest to the anode is reducing and hence behaves as a cathode. The opposite phenomenon occurs at the other floating electrode, making it an (oxidising) anode.

The potential profiles in the solution and at the platinum electrodes that result from the current transport are depicted in FIG. 8 for a steady state situation. In FIG. 8, the axis marked "x" indicates longitudinal position along the solution channel, i.e. in a direction parallel to the short circuit connection between the two electrodes. In the solution the potential gradient is linear, due to the solution's uniform ohmic resistance. The electrode's current path has a substantially zero internal potential drop and steep potential gradients at the interfaces with the solution.

The total ohmic resistance of the channel, $R_\Omega$ [Ω], is a function of the fluxes of all ionic species:

$$R_\Omega = \frac{RT}{F^2 \sum_i z_i^2 c_i D_i} \cdot \frac{l}{A}$$

where R, T and F have their usual meaning (R is the gas constant, T is the temperature and F is the Faraday constant), z is the ionic charge, c [mol m$^{-3}$] the species concentration, D [m$^2$s$^{-1}$] its diffusion coefficient, l [m] the channel length and A [m$^2$] the channel cross-sectional area.

In the platinum metal and the short circuit the potential gradient is negligible. Steep potential gradients, however, exist at the interfaces with the solution. These gradients are associated with the mass transfer overpotentials $\eta_{mt}$, and the standard potentials E$^0$ for the Faradeic reactions occurring.

If we assume that $i_2 \ll i_1$, than the electrical potential difference between the two Pt electrodes is $$\Delta U_{Pt} = \Delta U \frac{d_{Pt}}{l} = 0.09 \, \Delta U,$$

where l [m] is the channel length and $d_{Pt}$ the distance between the Pt electrodes. In the steady state situation $$(\eta_{mt} + E^0)_1 + (\eta_{mt} + E^0)_2 = \Delta U_{Pt}.$$

At the interfaces between solution and electrodes, those Faradeic reactions will occur, for which the potential difference between electrodes and solution exceeds their standard potential E$^0$. (Note that the average potential of the Pt versus the local potential of the solution is determined by the solution chemistry and will be somewhere between about +1 and −1 V). Possible Faradeic processes at the floating cathode and anode in the system, with the corresponding standard potentials E$^0$ are:

anode:

| | |
|---|---|
| [Ru(bp)$_3$]$^{2+}$ → [Ru(bp)$_3$]$^{3+}$ + e   E$^0$ vs. Ag/AgCl: | 1.3 |
| 2Cl$^-$ → Cl$_2$ + 2e | 1.13 |
| 2H$_2$O → 4H$^+$ + O$_2$ + 4e   (pH = 7) | 0.6 | cathode:

| | |
|---|---|
| e + [Ru(bp)$_3$]$^{2+}$ → [Ru(bp)$_3$]$^+$ | −1.3 |
| 4e + 2H$_2$O + O$_2$ → 4OH$^-$   (pH = 7)   about | −0.1 |
| 2e + H$_2$O → 2OH$^-$ + H$_2$   (pH = 7) | −0.65 |

The standard potentials, E$^0$, for a number of possible reactions are shown schematically in FIG. 9. The values given for the Ruthenium compounds are for solutions in acetonitrile, employing a Ag electrode as the reference and might differ a little when expressed vs. Ag/AgCl.

It can be seen that (at pH=7) oxidation of [Ru(bp)$_3$]$^{2+}$ occurs at a potential above that of anodic water electrolysis. Water oxidation and oxygen production, however, is kinetically slow at a Pt electrode and occurs in an appreciable measure only at potentials higher than that for Ru oxidation. [Ru(bp)$_3$]$^{3+}$ therefore can be produced in aqueous solution at a Pt electrode.

The reduction of [Ru(bp)$_3$]$^{2+}$ occurs at such negative potential that cathodic water electrolysis (and/or oxygen reduction) will interfere. Therefore non-aqueous media are used by authors who practise cathodic DC ECL or AC ECL.

Because it has a reduction potential of −0.8 V, [Ru(bpz)$_3$]$^{2+}$ has been used for cathodic DC ECL. With this compound, its high oxidation potential of +1.9 V makes it unsuitable for aqueous AC ECL.

The mass transfer overpotentials, $\eta_{mt}$ [V], at the interfaces of Pt electrodes and solution are not real electrical potential gradients, but electrical analogues for concentration gradients of the substances that are oxidised or reduced at the electrode. Likewise the associated mass transfer resistances are not real electrical resistances, but electrical analogues for the resistance that the system offers to mass transport towards the electrode.

To derive equations for these variables, the simplified schematic picture of the concentration gradients at the anode shown in FIG. 10 can be helpful. It employs the concept of the stagnant layer or Nernst diffusion layer. This concept simplifies calculations for flowing or stirred solutions, by simplifying the parabolic Poiseulle flow profile to a stationary solution layer of thickness δ adjacent to the wall and a plug flow profile in the bulk. The thickness δ is determined by the flow velocity or the stirring rate.

The mass-transfer overpotential can be expressed in terms of the concentration difference between electrode surface (x=0) and solution bulk (*) of the electrochemically active species. E.g., for the oxidation of substance R (Ru(II)) or TPA) at the anode we have

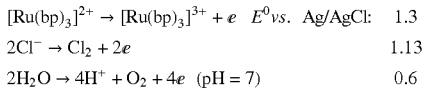

The overpotential thus increases with increasing depletion of the electroactive substance at the electrode surface. The mass transfer resistance, $R_{mt}$ [Ω], for the oxidised substance is $$R_{mt} = \frac{\delta}{[c_R^* - c_R(x=0)]DA} \cdot \frac{RT}{F^2} \ln \frac{c_R^*}{c_R(x=0)},$$

where δ [m] is the Nernst layer thickness. The mass transfer resistance can thus be decreased by decreasing δ (higher solution velocity) or by increasing the bulk concentration of the oxidised substance. Note that the resistance via the logarithmic term strongly increases when the substance R at the electrode surface gets depleted. The current through the Pt can be derived from the above equations as

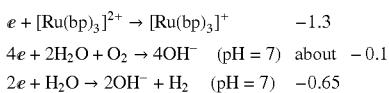

The current can be increased by decreasing δ and by increasing the bulk concentration of the oxidised substance R.

FIG. 11 schematically shows an equivalent electrical circuit describing steady-state current transport. $R_\Omega$ generally does not depend on the current, while $R_{mt}$ is strongly current dependent. The maximal (limiting) current through the floating electrodes occurs, when the surface concentration of the amine and Ruthenium compounds is zero:

$$i_{lim} = \frac{c_R * DAF}{\delta}.$$

At this value the maximal amount of light is produced. It is interesting to investigate theoretically if the system as described can deliver this current. For this the necessary condition is, that the total current is larger than the limiting current. The total current i equals $$i = \frac{F^2 \sum_i z_i^2 c_i D_i}{RT} \cdot \frac{AU}{l}.$$

The condition that $i > i_{lim}$ can thus be expressed as $$\frac{U}{\frac{RT}{F}} \cdot \frac{\sum_i z_i^2 c_i D_i}{c_R * D} \cdot \frac{\delta}{l} > 1.$$

Assuming as a worst case that the second term at the left-hand side equals 2 (if only TPA ions contribute), we obtain:

$$\frac{U}{\frac{RT}{F}} \cdot 2 \cdot \frac{\delta}{l} > 1.$$

Taking U=20 V, δ=20 μm, l=76 mm and RT/F=25 mV, the right-hand term equals 0.42. This means that in the present system possibly the limiting current cannot be reached. However, we are relatively safe since i will be higher due to the presence of the phosphate buffer, and because a sizeable current is all that we need, not the limiting current.

The potential of the cathode in the present system is fixed either by oxygen reduction or water reduction. In further embodiments of the invention its potential could be better set by offering a background concentration of another oxidant (such as tertiary amines, aliphatic tertiary amines, secondary amines or primary amines in combination with divinylsulfone). The cathode then will act like a pseudo-reference electrode against which we can exactly fix the potential of the anode. No reference electrode is needed in this embodiment.

Effect of Distance on Voltage on Floating Electrode

The voltage difference across the two floating electrodes is directly proportional to the distance between the two given electrode and the voltage applied across the inlet and outlet of the channel. The observed voltage in the following table support this argument, when the distance between the two hydrostatically and electrically floating electrodes increases the voltage difference across these floating electrodes increases until the floating electrodes touches the electrodes in the outlet and inlet. At this point the voltage applied across the channel is the same as the voltage applied at the floating electrode and the electrode ceases to be electrically floating.

On the other hand, when the distance between the floating electrodes decreases, the voltage across these electrodes decreases. If these electrodes are connected together via external connection, this causes a short circuit in the solution and at this point the electrodes toward the anode behave like a cathode and the electrode facing the cathode behave like an anode. If these two electrodes are connected via an ammeter the changes in current can be measured which indicates the progress of the chemical reaction. This experiment has been performed on prototype embodiments and the results for three distance values (19 mm, 10.5 mm and 6.5 mm) are shown in FIG. 12. The resultant light is measured to detect the concentration of light emitting labelled analytes.

Stability Over Time

In the flowing solution the voltage across the floating electrode is stable because the solution in the vicinity of the electrodes are changing constantly and a kind of equilibrium formed among the oxidised and reduced species which stabilises the voltage difference across the floating electrode.

In a non-flow situation the concentration of oxidised and reduced species in the solution in the vicinity of the electrode will change with time which will alternatively change the voltage difference between floating electrode. Although these species will move away from the electrodes by diffusion but this will not be enough to form the equilibrium among the oxidised and reduced species. Therefore the stable voltage across the floating electrode will be hard to achieve.

FIG. 13 illustrates changes in voltage between the floating electrodes with time when the solution is flowing at 15 μL per second. FIG. 14 illustrates changes in voltage between the floating electrodes with time when the solution is not flowing. It can easily be seen that the voltage is much more stable when the solution is flowing, so preferred arrangements use flowing solution.

The following table provides a calibration curve for the concentration of TBR:

| Concentration (M) | Light Intensity Arbitrary Units |
|---|---|
| 1.0E−10 | 1 |
| 2.0E−10 | 2.1 |
| 5.0E−10 | 6 |
| 1.0E−09 | 13 |
| 5.0E−09 | 63 |
| 1.0E−08 | 126 |
| 3.0E−08 | 610 |
| 1.0E−07 | 1240 |
| 5.0E−07 | 6400 |
| 1.0E−06 | 13500 |

The light generation on the surface electrodes increases with increase in the flow rate of the TBR/TPA solution. This is because the number of ions passes and oxidised at the surface of electrode increases with flow rate and also the higher flow rate stabilise the voltage at the working (floating) electrode by forming the equilibrium in the vicinity. Results obtained for the prototype embodiment are shown in FIG. 15.

FIG. 16 illustrates the light intensity obtained with the prototype embodiment against the voltage applied across the inlet and outlet of the flow cell.

Further possible embodiments will now be described, some with reference to FIGS. 17 and 18.

FIG. 17 is a schematic plan view of a further embodiment, in which a two-dimensional array of, for example, 100×100 floating gold electrodes 400, each 50 mm×50 mm×50 μm is disposed between two elongate anode 410 and cathode 420 electrodes connected to a power supply. Pairs of the electrodes spaced apart in the flow direction may be short-circuited together as described above.

FIG. 18 takes this one step further, with a three-dimensional array 430 of electrodes shown in side elevation. Further floating electrodes 440 of the type described with reference to FIG. 2 are also provided.

In general, single electrodes, 1-, 2- or 3-dimensional arrays of electrodes or free-form groups of electrodes (such as 5 μm diameter gold, platinum or other metal particles, metal-coated particles or conductive polymer particles in suspension), either interconnected or free, can be used. The dimensions of the electrodes are not bounded except by the particular reaction vessel in use, but preferred limits are: 50 nm–1 mm in the direction of the electric field, and 50 nm–5 cm in other directions.

The reaction vessel or detection volume can be a channel as shown in FIG. 2, a plate-like shape as shown in FIG. 17, a volume capable of enclosing a 3-d array of electrodes as shown in FIG. 18, and so on. In general, any type of volume such as a channel (particularly a channel provided on an integrated chip), a microvial, a cuvette and so on.

The externally-supplied electric field can be dc (as shown in FIG. 2) but could instead be pulsed dc or ac (with or without a dc component). A further alternative arrangement using inductive generation of an electric field will be described below with reference to FIG. 20.

At least some of the electrodes can be coated in suitable materials for bio-sensing or chemical sensing, such as thiol linked antibodies, DNA probes or other molecules immobilised on the electrodes surface. (See, for example, Rampi M A et al, Applied Physics Letters, 1998, 72, No 14, pp 1781–1783 and Qin D et al, Topics in Current Chemistry, 1998, 194, pp1–20). Other test or analysis agents can be provided in solution, such as Ru-labelled calibrants. In particular, if a known amount of an Ru-labelled calibrant is provided along with an unknown amount of an analyte molecule and competition assay is allowed to take place, the amount of the unknown analyte can be assessed.

Any standard immunoassay, DNA hybridisation assay, receptor based assay, enzyme inhibition assay, protein-protein binding assay and many more can be performed by replacing the fluorescence or radioactive label normally used in such procedures by an ECL label, for example Ru(bpy)$_3$ or other known compounds. FIG. 19a schematically shows a DNA binding assay in a direct detection format, where the probe DNA 500 is directly bound to the metal surface and the successful binding results in a Ru label 510 being close to the electrode 520 to emit light. Alternatively the binding site 530 can be separate from the electrode 540 but nearby to allow detection of any trapped (bound) and released material from the binding site (see FIG. 19b).

These binding sites can be arranged in a similar way to those in Fodor S P A et al, Science, 251, pp767–773 (1991). DNA or other chemical species can be selectively bound to one or a few electrodes only to give a large array of similar but not identical probes. A given location of detection identifies a defined assay.

Combinatorial bioassays can be carried out by preparing small batches of metal, metal coated or conductive polymer beads with a specific molecular probe immobilised on their surface. They can be mixed together to carry out all of the provided assays randomly. The successful assays can be detected and separated out using flow cytometry. Alternatively, several experiments can be carried out with sub-sets of particles to find out in which batch(es) the successful assay is obtained. The basic principles behind these methods are standard within combinatorial is synthesis.

FIG. 20 illustrates an arrangement using inductive generation of an electric field within a reaction vessel 600. Particulate electrodes 610 are disposed in suspension in a conductive solution within the reaction vessel, and an alternating magnetic field created by driving an external coil 620 generates an electric field within the vessel, causing the electrodes to become polarised as described above.

FIG. 21 is a general schematic illustration showing the use of discrete particulate reaction electrodes in suspension in a current flow path between two supply electrodes. The face of each reaction electrode towards the supply anode becomes an oxidising surface, and that towards the supply cathode becomes a reducing surface. If an ac supply is used, these roles alternate with the current polarity.

FIGS. 22a to 22c schematically illustrate three different configurations of particulate electrodes. In FIG. 22a, the electrodes are distributed quasi-continuously throughout the reaction vessel (or a region of it). Alternatively they can be injected as discrete plugs or groups (FIG. 22b) or as singles, well-spaced particles (FIG. 22c).

As another example of a further embodiment, a fused silica capillary normally used for electrophoresis or electrochromatography separation can be employed. Metal particles (5 μm diameter) are placed in the capillary and a voltage applied across the channel, and the resulting light emission can be detected using a photomultiplier. An example set of results from such an apparatus is illustrated in FIG. 23.

As a further example, a capillary formed on a planar glass substrate and normally used for electrophoresis separation is used, with an integrated metal electrode array provided across the channel. Light detection can be performed using a camera.

It will be apparent that features of these different embodiments can be combined, for example a disposition of electrodes from one embodiment can be combined with a reaction vessel from another embodiment.

What is claimed is:

1. An electrochemiluminescence apparatus, comprising:
a reaction vessel for containing a conductive solution;
electric field generation means for generating an electric field within at least a region of the reaction vessel when it contains a conductive solution; and
at least one set of two or more reaction electrodes disposed in the electric field region of the reaction vessel, the reaction electrodes of the at least one set being spaced apart in the reaction vessel and electrically connected to one another by connection means other than a conductive solution in the reaction vessel, the reaction electrodes being arranged to be electrically floating with respect to the means for generating the electric field.

2. An apparatus according to claim 1, wherein the electric field generation means comprises first and second supply electrodes connectable to an electric power supply for developing a flow of electric current in a conductive solution in the reaction vessel between the supply electrodes and thereby provide an electric field within the electric field region of the reaction vessel.

3. An apparatus according to claim 2, wherein the power supply is a direct current power supply.

4. An apparatus according to claim 1, wherein the electric field generation means comprises an alternating magnetic field generation means within the reaction vessel and thereby induce an electric field within the electric field region of the reaction vessel.

5. An apparatus according to claim 1, wherein the reaction electrodes of each set are electrically short-circuited by a conductive element.

6. An apparatus according to claim 5, wherein the conductive element is a wire.

7. An apparatus according to claim 1, wherein at least one of the reaction electrodes is formed such that it hydrostatically floats in use in or on a conductive solution in the reaction vessel.

8. An apparatus according to claim 1, wherein the at least one set of reaction electrodes comprises a 1-, 2-, or 3-dimensional array of reaction electrodes.

9. An apparatus according to claim 1, wherein the reaction electrodes are metal particles, metal-coated particles or conductive polymer particles.

10. An apparatus according to claim 1, wherein the at least one set of reaction electrodes is provided by a metal wire.

11. An apparatus according to claim 1, wherein the reaction vessel includes a solution inlet and a solution outlet, and the apparatus further comprises flow means for causing a conductive solution to flow through the reaction vessel from the inlet towards the outlet.

12. An apparatus according to claim 11, wherein the flow means comprises a pump.

13. An apparatus according to claim 1, wherein the reaction vessel is an elongate channel.

14. An apparatus according to claim 13, wherein the reaction vessel is an electrophoretic migration channel.

15. An apparatus according to claim 1, wherein at least one of the reaction electrodes is coated with a bio-sensing or chemical-sensing coating.

16. An apparatus according to claim 1, comprising a plurality of sets of reaction electrodes.

17. An apparatus according to claim 15, wherein each set of reaction electrodes is coated with a respective type of sensing coating.

18. An apparatus according to claim 1, further comprising a photomultiplier detector for detecting optical emission from within the reaction vessel.

* * * * *